(12) United States Patent
Robinson et al.

(10) Patent No.: US 12,102,604 B1
(45) Date of Patent: Oct. 1, 2024

(54) MEDICAL APPARATUS

(71) Applicant: SOUNCALINK, LLC, Temecula, CA (US)

(72) Inventors: David C. Robinson, Temecula, CA (US); Matthew D. Robinson, Temecula, CA (US)

( * ) Notice: Subject to any disclaimer, the term of this patent is extended or adjusted under 35 U.S.C. 154(b) by 0 days.

(21) Appl. No.: 18/542,191

(22) Filed: Dec. 15, 2023

(51) Int. Cl.
*A61J 7/00* (2006.01)
*A61J 1/16* (2023.01)

(52) U.S. Cl.
CPC ............... *A61J 7/0076* (2013.01); *A61J 1/16* (2013.01); *A61J 2205/60* (2013.01)

(58) Field of Classification Search
CPC ......... A61J 7/0076; A61J 1/16; A61J 2205/60
USPC ........................................................ 221/258
See application file for complete search history.

(56) References Cited

U.S. PATENT DOCUMENTS

| | | | | |
|---|---|---|---|---|
| 6,155,454 A | * | 12/2000 | George | A61J 7/0076 221/25 |
| 6,163,736 A | * | 12/2000 | Halfacre | A61J 7/0481 221/185 |
| 6,415,202 B1 | * | 7/2002 | Halfacre | A61J 7/0481 221/185 |
| 8,032,252 B2 | | 10/2011 | Berg | |
| 8,108,068 B1 | | 1/2012 | Boucher et al. | |
| 8,600,548 B2 | | 12/2013 | Bossi et al. | |
| 9,913,778 B2 | | 3/2018 | Dvorak et al. | |
| 10,392,181 B2 | | 8/2019 | Zonana et al. | |
| 11,676,693 B2 | | 6/2023 | Mercolino et al. | |
| 2006/0161295 A1 | | 7/2006 | Yun | |

(Continued)

FOREIGN PATENT DOCUMENTS

| | | | | |
|---|---|---|---|---|
| CN | 2841565 Y | * | 11/2006 | ............. B25H 3/022 |
| CN | 105291079 A | * | 2/2016 | ............. B25H 3/022 |

(Continued)

OTHER PUBLICATIONS

Jugeon Pak, Keehyun Park, Construction of a smart medication dispenser with high degree of scalability and remote manageability, PubMed, Jul. 26, 2012. https://pubmed.ncbi.nlm.nih.gov/22899886/.

(Continued)

*Primary Examiner* — Rakesh Kumar
(74) *Attorney, Agent, or Firm* — CIONCA IP Law P.C.

(57) ABSTRACT

A medical apparatus having a plurality of medical vials, each medical vial having a vial flange; and a medical carousel configured to be selectively engaged with the plurality of medical vials, the medical carousel having: a carousel platform having: a plurality of vial holders, wherein each vial holder is configured to be selectively engaged with a corresponding medical vial, each vial holder being configured to selectively confine the vial flange of the corresponding medical vial such that upon rotation of the medical vial about a vial vertical axis, and subsequent lifting of the medical vial, the vial holder is configured to allow a patient to extract the selected medical vial using an extraction tool. The medical apparatus may be configured to selectively rotate the medical carousel to align a corresponding medical vial with an extraction aperture, and actuate an extraction door to uncover the extraction aperture, thus facilitating medication dispensing.

19 Claims, 17 Drawing Sheets

(56) References Cited

U.S. PATENT DOCUMENTS

| | | |
|---|---|---|
| 2009/0192648 A1 | 7/2009 | Namineni et al. |
| 2010/0228566 A1 | 9/2010 | Taylor et al. |
| 2016/0022541 A1 | 1/2016 | Dalal et al. |
| 2016/0158107 A1* | 6/2016 | Dvorak ................ A61J 7/0084 221/9 |
| 2016/0283691 A1* | 9/2016 | Ali .......................... G16H 20/13 |
| 2019/0189307 A1* | 6/2019 | Mehrotra ............. G05B 19/042 |
| 2020/0279632 A1* | 9/2020 | Mercolino ............ A61J 7/0084 |
| 2020/0335192 A1 | 10/2020 | Tupler et al. |
| 2020/0390210 A1* | 12/2020 | Tsai ..................... B65D 81/113 |
| 2021/0249112 A1 | 8/2021 | Mercolino et al. |
| 2022/0105008 A1* | 4/2022 | Long .................... A61J 7/0454 |
| 2022/0402696 A1* | 12/2022 | Mercolino ............. G16H 40/67 |
| 2023/0147994 A1* | 5/2023 | Mercolino ............. G16H 40/63 700/240 |
| 2023/0351827 A1* | 11/2023 | Poddar ..................... A61J 1/16 |

FOREIGN PATENT DOCUMENTS

| | | | | |
|---|---|---|---|---|
| DE | 0758110 B1 * | 6/1996 | ............... | G06F 1/16 |
| DE | 202005012814 U1 * | 12/2005 | ............. | A45C 13/02 |
| DE | 102017209469 A1 * | 12/2018 | ................ | A61J 1/16 |
| EP | 3784198 B1 | 3/2023 | | |
| WO | 2014006620 A4 | 1/2014 | | |
| WO | WO-2014006620 A1 * | 1/2014 | ........... | A61J 7/0076 |
| WO | 2020092651 A1 | 5/2020 | | |

OTHER PUBLICATIONS

Pei-Hsuan Tsai, Tsung-Yen Chen, Chi-Ren Yu, Chi-Sheng Shih, Jane W.S. Liu, Smart Medication Dispenser: Design, Architecture and Implementation, ResearchGate, Apr. 2011, https://www.researchgate.net/publication/224177659_Smart_Medication_Dispenser_Design_Architecture_and_Implementation.

Diaa Salama Abdul Minaam, Mohamed Abd-Elfattah, Smart drugs: Improving healthcare using Smart Pill Box for Medicine Reminder and Monitoring System, ScienceDirect, Nov. 29, 2018, https://www.sciencedirect.com/science/article/pii/S2314728818300230.

* cited by examiner

MEDICAL APPARATUS

BACKGROUND OF INVENTION

1. Field of the Invention

The invention relates generally to medical apparatuses and specifically to apparatuses configured to facilitate secure handling and automated dispensing of medicine.

2. Description of the Related Art

It has become commonplace in the current healthcare landscape for individuals seeking medical care for their ailments to pursue medical assistance through telemedicine/telehealth practices, rather than actively traveling to a doctor's office or emergency care facility. While current telemedicine systems may ease the travel burden on a patient by allowing them to speak with a doctor/physician from the comfort of their own home, gaps still exist for current telemedicine systems and limit the quality of care enabled by current telemedicine practices.

One notable limitation of current telemedicine systems is the limited amount of diagnostic information the doctor may be able to collect from a patient during a digital meeting. The amount of diagnostic information that can be collected from a patient in their home is significantly less than the diagnostic information that can be collected in a doctor's office. In most cases, patients will not have access to even basic diagnostic devices, thus leaving the doctor reliant upon patient testimony and what they can observe/perceive through a video/phone call to make a diagnosis. Another notable limitation that exists for telemedicine practices is that even after a patient is diagnosed, and a medication is prescribed, said patient must perform additional steps and wait additional time to receive the medication required to be treated. This may entail traveling to a pharmacy, awaiting a delivery, or forcing a patient to go to the emergency room for treatment. As a result of these limitations, the quality of care provided to a patient utilizing telemedicine may not meet the same standard set forth by conventional, in-office doctor visits/emergency room visits.

Therefore, there is a need to solve the problems described above by proving a device and method for a secure medical apparatus configured to dispense prescribed medications to patients in real-time.

The aspects or the problems and the associated solutions presented in this section could be or could have been pursued; they are not necessarily approaches that have been previously conceived or pursued. Therefore, unless otherwise indicated, it should not be assumed that any of the approaches presented in this section qualify as prior art merely by virtue of their presence in this section of the application.

BRIEF INVENTION SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In an aspect, a medical apparatus is provided, the medical apparatus comprising: a top compartment having a plurality of foam pockets configured to securely house corresponding diagnostic devices; a bottom compartment configured to be pivotally engaged with the top compartment, the bottom compartment comprising: a bottom compartment body; a carousel receptacle nested within the bottom compartment body; a plurality of medical vials configured to be selectively nested within the carousel receptacle, each medical vial of the plurality of medical vials having: a vial body; a vial cap configured to be selectively engaged with the vial body to secure a medication within the vial body; and a vial flange affixed to the vial body, wherein the vial flange is configured to protrude away from a vial vertical axis, such that an about 90 degree flange angle is formed; and a medical carousel configured to be nested within the carousel receptacle and selectively engaged with the plurality of medical vials, the medical carousel comprising: a two layered carousel platform having: a plurality of vial holders, wherein each vial holder is configured to be selectively engaged with a corresponding medical vial of the plurality of medical vials, each vial holder of the plurality of vial holders comprising: a flange cavity configured to selectively confine the vial flange of a corresponding medical vial of the plurality of medical vials, such that the vial flange of the corresponding medical vial is securely nested within the flange cavity; and a flange slot associated with the flange cavity, wherein the flange slot is configured to allow the vial flange of the corresponding medical vial to be selectively removed from the flange cavity upon rotation of the corresponding medical vial about the corresponding vial vertical axis; and a motor configured to be pivotally engaged with the carousel platform, the motor being further configured to selectively rotate the carousel platform about a carousel rotational axis; a carousel cover configured to be engaged with the carousel receptacle, such that the medical carousel is enclosed within the carousel receptacle, the carousel cover having an extraction aperture; and an extraction door attached to the carousel cover, wherein the extraction door is configured to selectively cover the extraction aperture; and an extraction tool configured to be inserted through the extraction aperture to selectively engage with a corresponding medical vial of the plurality of medical vials for selective extraction of the corresponding medical vial from the medical carousel. Thus, an advantage is that the medical apparatus may be in data communication with the doctor's devices, such that information collected from the medical apparatus may be securely obtained by the doctor, and commands issued by the doctor may be immediately executed by the medical apparatus in the patient's possession. Another advantage is that upon receiving a diagnosis from a doctor, the medical apparatus may be configured to dispense a prescribed medication in real-time, thus allowing the patient to receive immediate treatment for their ailment for at minimum the critical first twenty four hours. Another advantage is that the medical apparatus may be configured to securely hold each medical vial, such that all medications may be securely held within the medical apparatus, thus preventing the held medicine from being dislodged from the medical apparatus through tampering and accidental impacts. Another advantage is that the medical apparatus may be configured to contain a wide variety of medications used to treat common illnesses, thus allowing for a singular medical apparatus to treat patients having a wide variety of conditions.

In another aspect, a medical apparatus is provided, the medical apparatus comprising: a bottom compartment body; a carousel receptacle nested within the bottom compartment body; a plurality of medical vials configured to be selectively nested within the carousel receptacle, each medical vial of the plurality of medical vials having: a vial body; a vial cap configured to be selectively engaged with the vial body to secure a medication within the vial body; and a vial flange secured to the vial body, wherein the vial flange is configured to protrude away from a vial vertical axis; and a medical carousel configured to be nested within the carousel receptacle and selectively engaged with the plurality of medical vials, the medical carousel comprising: a carousel platform having: a plurality of vial holders, wherein each vial holder is configured to be selectively engaged with a corresponding medical vial of the plurality of medical vials, each vial holder of the plurality of vial holders comprising: a flange cavity configured to selectively confine a vial flange of a corresponding medical vial of the plurality of medical vials, such that the vial flange of the corresponding medical vial is nested within the flange cavity; and a flange slot associated with the flange cavity, wherein the flange slot is configured to allow the vial flange of the corresponding medical vial to be selectively removed from the flange cavity upon rotation of the corresponding medical vial about the corresponding vial vertical axis; and a motor configured to be pivotally engaged with the carousel platform, the motor being further configured to selectively rotate the carousel platform on a carousel rotational axis; a carousel cover configured to be engaged with the carousel receptacle, such that the medical carousel is enclosed within the carousel receptacle, the carousel cover having an extraction aperture; and an extraction door attached to the carousel cover, wherein the extraction door is configured to selectively cover the extraction aperture. Again, an advantage is that the medical apparatus may be in data communication with the doctor's devices, such that information collected from the medical apparatus may be securely obtained by the doctor, and commands issued by the doctor may be immediately executed by the medical apparatus. Another advantage is that upon receiving a diagnosis from a doctor, the medical apparatus may be configured to dispense a prescribed medication in real-time, thus allowing the patient to receive immediate treatment for their ailment. Another advantage is that the medical apparatus may be configured to securely hold each medical vial, such that all medications may be securely held within the medical apparatus, thus preventing the held medicine from being dislodged from the medical apparatus through tampering and accidental impacts. Another advantage is that the medical apparatus may be configured to contain a wide variety of medications used to treat common illnesses, thus allowing for a singular medical apparatus to treat patients having a wide variety of conditions.

In another aspect, a medical apparatus is provided, the medical apparatus comprising: a plurality of medical vials, each medical vial of the plurality of medical vials having: a vial body; a vial cap configured to be selectively engaged with the vial body to secure a medication within the vial body; a vial flange affixed to the vial body, wherein the vial flange is configured to extend away from a vial vertical axis; and a medical carousel configured to be selectively engaged with the plurality of medical vials, the medical carousel comprising: a carousel platform having: a plurality of vial holders, wherein each vial holder of the plurality of vial holders is configured to be selectively engaged with a corresponding medical vial of the plurality of medical vials, each vial holder of the plurality of vial holders comprising: a flange cavity configured to selectively confine a vial flange of a corresponding medical vial, such that the vial flange of the corresponding medical vial is nested within the flange cavity; and a flange slot associated with the flange cavity, wherein the flange slot is configured to allow the vial flange of the corresponding medical vial to be selectively removed from the flange cavity upon rotation of the corresponding medical vial about the corresponding vial vertical axis. Again, an advantage is that the medical apparatus may be in data communication with the doctor's devices, such that information collected from the medical apparatus may be securely obtained by the doctor, and commands issued by the doctor may be immediately executed by the medical apparatus. Another advantage is that upon receiving a diagnosis from a doctor, the medical apparatus may be configured to dispense a prescribed medication in real-time, thus allowing the patient to receive immediate treatment for their ailment. Another advantage is that the medical apparatus may be configured to securely hold each medical vial, such that all medications may be securely held within the medical apparatus, thus preventing the held medicine from being dislodged from the medical apparatus through tampering and accidental impacts. Another advantage is that the medical apparatus may be configured to contain a wide variety of medications used to treat common illnesses, thus allowing for a singular medical apparatus to treat patients having a wide variety of conditions.

The above aspects or examples and advantages, as well as other aspects or examples and advantages, will become apparent from the ensuing description and accompanying drawings.

BRIEF DESCRIPTION OF THE DRAWINGS

For exemplification purposes, and not for limitation purposes, aspects, embodiments or examples of the invention are illustrated in the figures of the accompanying drawings, in which.

DETAILED DESCRIPTION

Figure 1A:
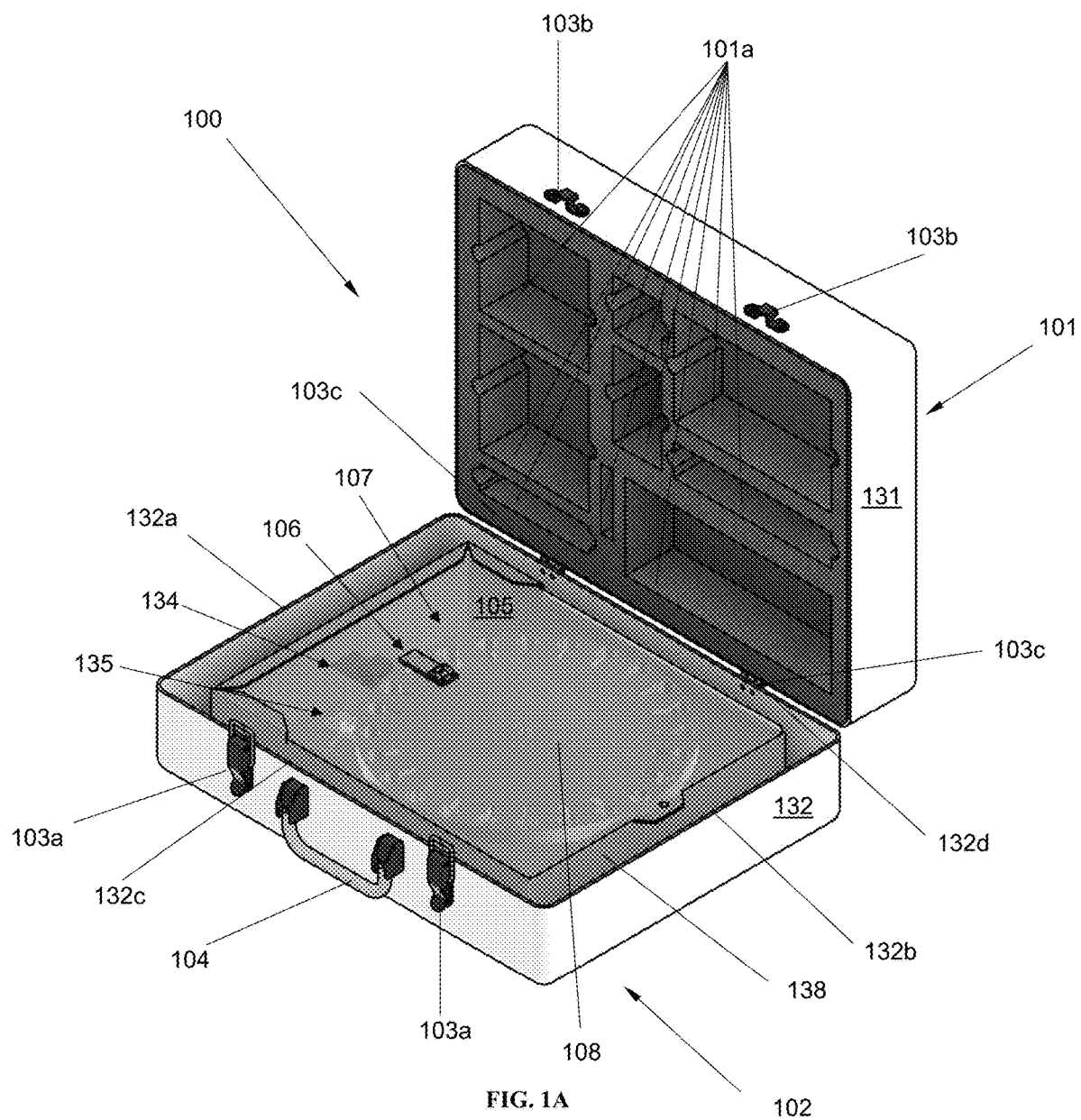
FIGS. 1A-1D illustrate the top perspective, top exploded, front elevation and top plan views, respectively, of a medical apparatus, according to an aspect.

What follows is a description of various aspects, embodiments and/or examples in which the invention may be practiced. Reference will be made to the attached drawings, and the information included in the drawings is part of this detailed description. The aspects, embodiments and/or examples described herein are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

It should be understood that, for clarity of the drawings and of the specification, some or all details about some structural components or steps that are known in the art are not shown or described if they are not necessary for the invention to be understood by one of ordinary skills in the art.

As used herein and throughout this disclosure, the term "mobile device" refers to any electronic device capable of communicating across a mobile network. A mobile device may have a processor, a memory, a transceiver, an input, and an output. Examples of such devices include cellular telephones, personal digital assistants (PDAs), portable computers, etc. The memory stores applications, software, or logic. Examples of processors are computer processors (processing units), microprocessors, digital signal processors, controllers and microcontrollers, etc. Examples of device memories that may comprise logic include RAM (random access memory), flash memories, ROMS (read-only memories), EPROMS (erasable programmable read-only memories), and EEPROMS (electrically erasable programmable read-only memories). A transceiver includes but is not limited to cellular, GPRS, Bluetooth, GPS and Wi-Fi transceivers.

"Logic" as used herein and throughout this disclosure, refers to any information having the form of instruction signals and/or data that may be applied to direct the operation of a processor. Logic may be formed from signals stored in a device memory. Software is one example of such logic. Logic may also comprise digital and/or analog hardware circuits, for example, hardware circuits comprising logical AND, OR, XOR, NAND, NOR, and other logical operations. Logic may be formed from combinations of software and hardware. On a network, logic may be programmed on a server or a complex of servers. A particular logic unit is not limited to a single logical location on the network.

Mobile devices communicate with each other and with other elements via a network, for instance, a cellular network. A "network" can include broadband wide-area networks, local-area networks, and personal area networks. Communication across a network can be packet-based or use radio and frequency/amplitude modulations using appropriate analog-digital-analog converters and other elements. Examples of radio networks may include GSM, CDMA, Wi-Fi and BLUETOOTH® networks and any current or future technology yet to be developed, with communication being enabled by transceivers. A network typically includes a plurality of elements such as servers that host logic for performing tasks on the network. Servers may be placed at several logical points on the network. Servers may further be in communication with databases and can enable communication devices to access the contents of a database. For instance, an authentication server hosts or is in communication with a database having authentication information for users of a mobile network. A "user account" may include several attributes for a particular user, including a unique identifier of the mobile device(s) owned by the user, relationships with other users, call data records, bank account information, etc. A billing server may host a user account for the user to which value is added or removed based on the user's usage of services. One of these services includes mobile payment. In exemplary mobile payment systems, a user account hosted at a billing server is debited or credited based upon transactions performed by a user using their mobile device as a payment method.

For the following description, it can be assumed that most correspondingly labeled elements across the figures (e.g., 108 and 208, etc.) possess the same characteristics and are subject to the same structure and function. If there is a difference between correspondingly labeled elements that is not pointed out, and this difference results in a non-corresponding structure or function of an element for a particular embodiment, example or aspect, then the conflicting description given for that particular embodiment, example or aspect shall govern.

FIGS. 1A-1D illustrate the top perspective, top exploded, front elevation and top plan views, respectively, of a medical apparatus 100, according to an aspect. In an embodiment, a medical apparatus ("diagnosing dispenser," "medical dispenser," "mobile diagnostic and automated medication dispensing apparatus") 100 is provided. This medical dispenser 100 may be a diagnostic and/or therapeutic device which may have the approximate size and shape of a standard attaché case or briefcase (or other similarly sized storage unit). Said medical dispenser 100 may be placed in the home of a patient, but may be suitably sized to take along with patients as they travel, due to its manageable size. Through the utilization of suitable communications technologies, the medical dispenser 100 may be configured to provide telehealth standards of medical care worldwide between patients and doctors using a patient's smart-phone network (e.g., 3G, 5G, etc.), a Wi-Fi/Bluetooth connection, or any other suitable type of network connection.

Figure 1B:
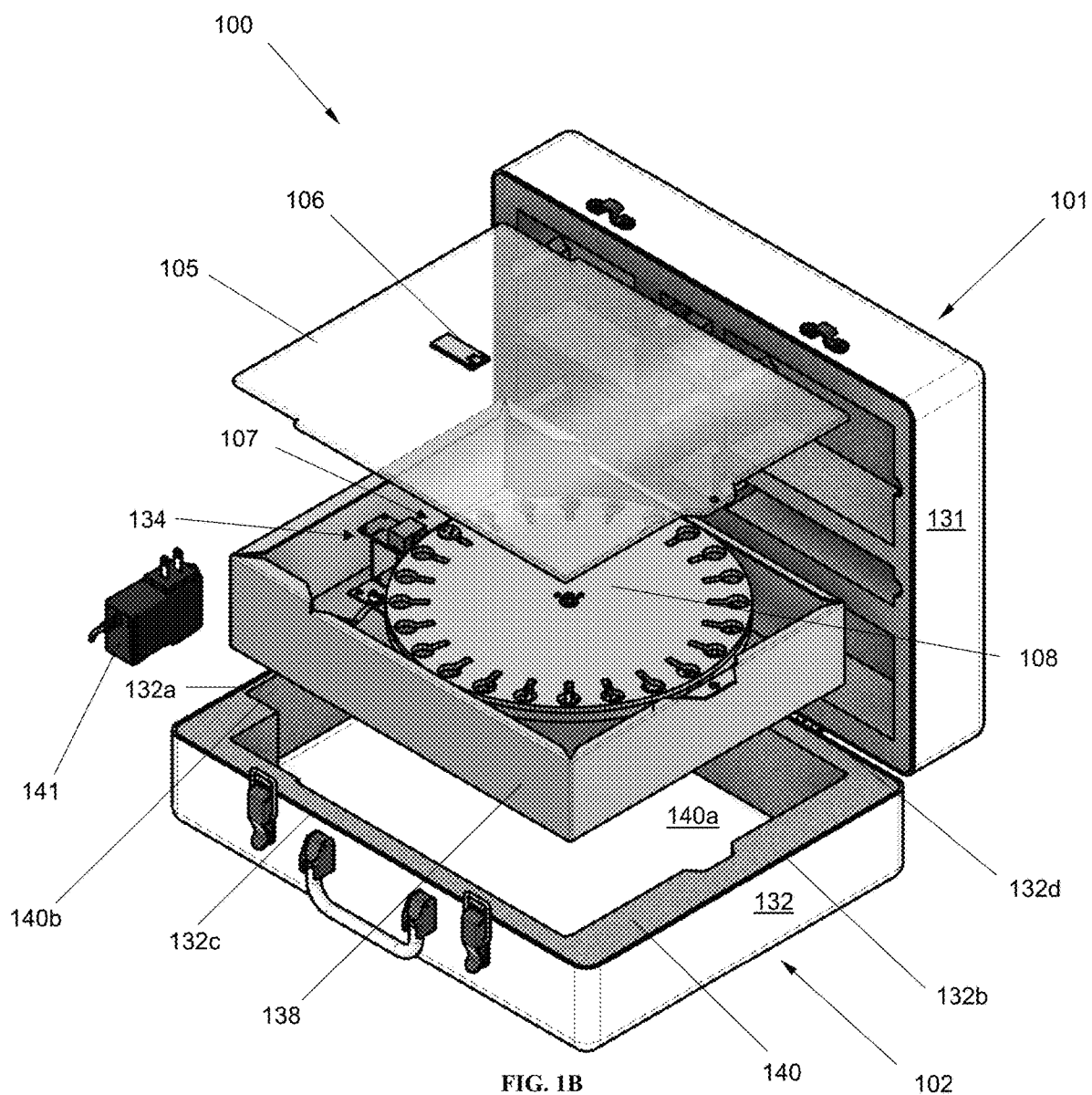
Figure 1C:
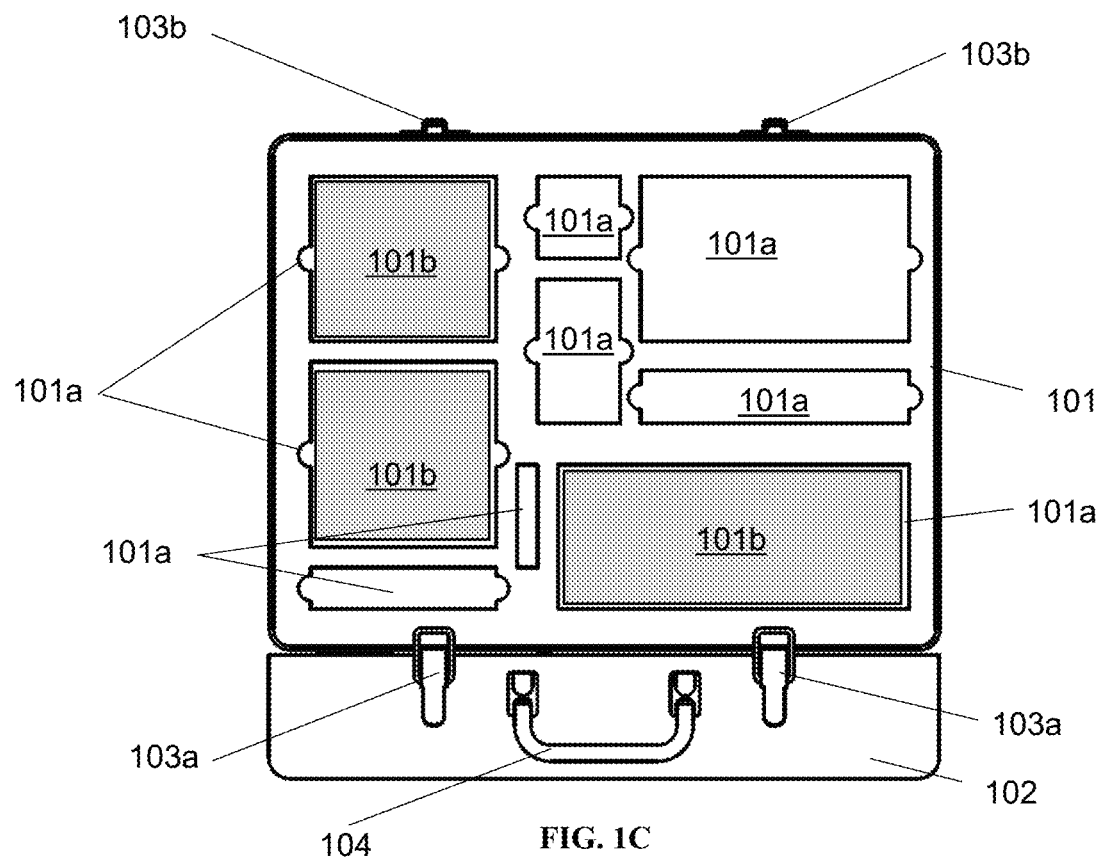
Figure 1D:
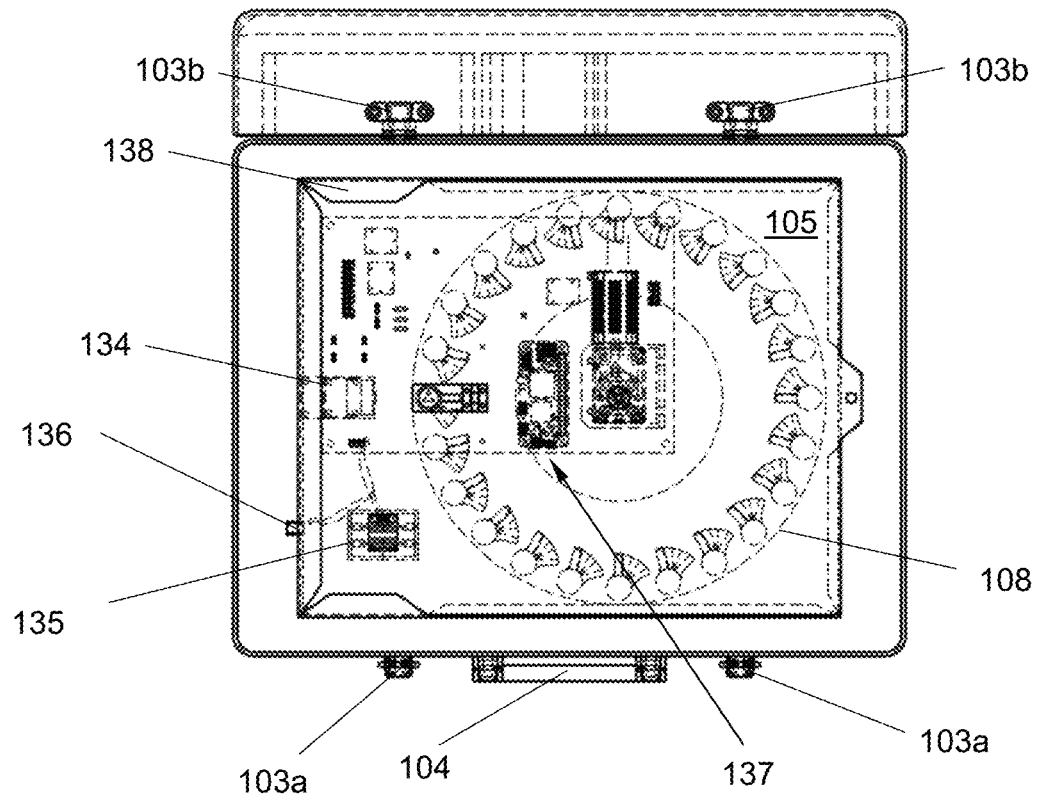

In an embodiment, the medical dispenser 100 may comprise two compartments: a top compartment 101 and a bottom compartment 102, wherein the two compartments together form an attaché case. The top compartment 101 may be configured to pivotally engage with the bottom compartment 102 using a pair of riveted rear hinges 103c, such that the medical dispenser 100 may be opened or closed via manipulation of a pair of latch arms 103a, wherein each latch arm 103a is configured to be selectively and reversibly engaged with a corresponding latch hook 103b. The top compartment 101 may have a top compartment body 131 within which its corresponding structures and elements may be stored, whereas the bottom compartment 102 may have a bottom compartment body 132 within which its corresponding structures and elements may be stored, wherein pivotal engagement between the top compartment body 131 and the bottom compartment body 132 may form a structure similar to an attaché case, as seen in FIG. 1A-1B. In an embodiment, the top compartment 101 may be further secured to the bottom compartment 102 by a corresponding keyed lock/suitcase lock (not shown), thus ensuring only authorized users are allowed to utilize the medical dispenser 100. In an embodiment, a carrying handle 104 may be secured to the bottom compartment 102 to facilitate easy transport of the medical dispenser 100.

In an embodiment, the top compartment 101 may comprise a plurality of diagnostic devices 101b and non-pharmaceutical treatment modalities. The top compartment 101 may have a plurality of firm foam pockets 101a, wherein each foam pocket 101a is configured to be precisely sized and fitted to securely house or otherwise engage with a corresponding diagnostic device 101b and/or other devices. In an embodiment, these corresponding devices may comprise diagnostic devices 101b including, but not limited to: a Kardia-EKG device having one or more leads and Bluetooth connectivity or equivalent device, a blood pressure cuff, a peak flow meter, a glucometer, a fountain pen sized Bluetooth wireless camera configured with supplied different speculum to allow the patient to view the inner/outer ear, throat, lesions, or other body parts as deemed necessary by the treating provider, using the Bluetooth camera (e.g. an orifiscope or visual otoscope, such as a BeBird), a thermometer, pulse oximeter, measuring tape, and/or other diagnostic devices. Through utilization of various diagnostic devices held in the top compartment 101, patients may be capable of collecting relevant diagnostic information while away from the doctor's office/emergency room, thus providing physicians/providers with additional information for making accurate diagnoses.

In addition to the diagnostic devices, a plurality of the foam pockets 101a may be configured to house a number of lab tests and non-pharmaceutical treatment modalities, which may include (but not be limited to): pregnancy tests (HCG strips), urine tests strips (such as DIAGNOX, URINOX-10 UA strips and SOUNCA Rapid Urine Test Cards), Antibiotic ointment, Guiac cards to test for unseen blood usually the stool sample is tested, Guiac reagent to develop the Guiac card for +/−, popsicle sticks applicators (for stool or other samples), ammonia (smelling salts), tincture benzoin, Steri strips ¼"×1.5" (as well as other sizes), adhesive bandages (round, straight, butterfly, etc.), alcohol pads, COVID tests and/or other diagnostic tests/therapeutic treatments. In an embodiment, data obtained from the diagnostic tools/devices 101b housed within the top compartment 101 may be recorded by a control app ("SOUNCALINK App", "control application") in communication with the medical dispenser 100. Said data may be provided to a physician/provider through the corresponding control app for review during a telehealth interview for more accurate diagnosis and treatment, thus meeting the standard of care substantially comparable to an in office visit.

In an embodiment, the medical dispenser 100 may be configured to transmit relevant device information, such as medication inventory, GPS location of the medical dispenser 100, and other data, utilizing onboard electronics configured to enable Wi-Fi and/or 3G connectivity without patient involvement or use of their smartphone/device. In an alternative embodiment, the medical dispenser 100 may utilize a connection (Bluetooth, Wi-Fi, etc.) with a patient's smartphone/device to facilitate transfer of relevant data from the medical dispenser 100 to doctor's offices, with or without the presence of the control application on the patient's smartphone/device. This control application will be discussed in greater detail hereinbelow.

In order to compliment the various diagnostic and therapeutic devices enclosed in the top compartment 101, the bottom compartment 102 may be configured to be electronically operated by the corresponding control application to dispense suitable medications to treat patient's ailments. As will be described in greater detail hereinbelow, a medical carousel ("acute care medicine dispensing device," "medication dispensing device," "MDD," "medication carousel") 107 may be housed, nested or otherwise enclosed within the bottom compartment body 132 of the bottom compartment 102. In an embodiment, the elements of the medical carousel 107 may be nested within a carousel receptacle 138, wherein the carousel receptacle 138 itself may be nested within the bottom compartment body 132. This carousel receptacle 138 may be configured to engage with a carousel cover 105 in order to securely enclose the medical carousel 107 within the carousel receptacle 138, such that a user may only access the medical carousel 107 (and this its contents) through an electronically locked extraction door 106 controlled by the medical dispenser 100. In an embodiment, the carousel cover 105 may be a riveted plexiglass top or other similar durable material.

By utilizing a carousel receptacle 138 having dimensions that are less than that of the surrounding bottom compartment body 132, a foam liner 140 may be inserted between the carousel receptacle 138 and the perimeter portions 132a, 132b, 132c, 132d of the bottom compartment body 132. In an embodiment, this foam liner 140 may have a receptacle pocket 140a within which the carousel receptacle 138 may be nested, for secure placement within the bottom compartment 102. The carousel receptacle 138 may be securely engaged with the bottom compartment body 132 by a flat lock, such as flat lock 1242 of FIG. 12A-12B, or another suitable locking mechanism, as will be disclosed in greater detail hereinbelow. The foam liner 140 may be helpful for protecting the medical carousel 107 and its held medications from accidental impacts by suitably cushioning the medical carousel 107 within the bottom compartment 102. In an embodiment, the carousel receptacle 138 may be made out of aluminum or another sufficient strong material, whereas the bottom compartment body 132 and the top compartment body 131 may be made out of a sufficiently durable metal or plastic to prevent damage from wear and tear and/or tampering attempts.

Figure 7A:
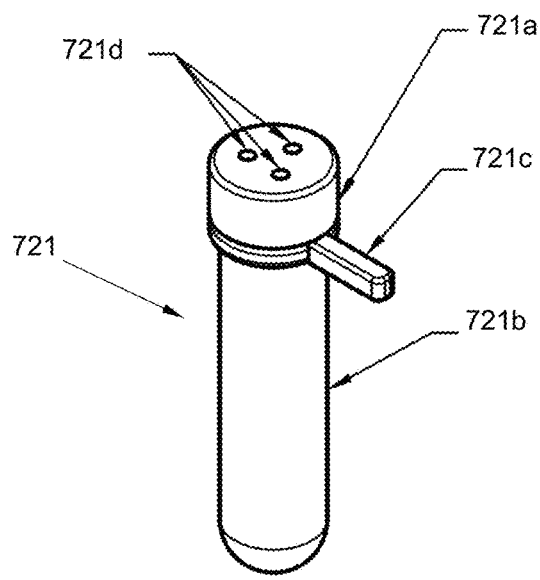
FIGS. 7A-7C illustrate the top perspective, side elevation and top plan views, respectively, of a medical vial, according to an aspect.

In an embodiment, the extraction door 106 may be attached to the carousel cover 105 and configured to only allow a patient access to a corresponding medical vial(s) secured within medical carousel 107, such as medical vial 721 of FIG. 7A, upon being diagnosed by a physician, to ensure that the patient is provided with the correct medication for their particular ailment. It should be understood that various sensors and devices, including security sensors and GPS devices (not shown), may also be stored within the bottom compartment 102, to ensure that these elements are suitably secured within the medical dispenser 100. In an embodiment, the medical carousel 107 and the extraction door 106 may be controlled by a corresponding control app, such as a SOUNCALINK App on a patient's device and/or the medical dispenser 100, wherein this application is configured to facilitate the delivery of medication to the patient in real-time, as will be described in greater detail hereinbelow. In an embodiment, the SOUNCALINK App may have a physician/provider side and a patient side, and be configured to allow for or otherwise facilitate video telehealth sessions, thus meeting a standard of care equal to an in person office visit. The SOUNCALINK App may be configured to connect patients and doctors via real-time video communication, while also communicating with the electromechanical functions of medical dispenser 100.

As disclosed hereinabove, the medical carousel 107 may be a secure, self-contained electro-mechanical automated medication dispensing device that enables a licensed telehealth physician (or mid-level provider) to dispense any number of medical vial(s) having medication from the medical dispenser 100, from a remote location via the SOUNCALINK App in real-time. In an embodiment, the medical carousel 107 may be configured to rotate a carousel platform 108 such that a medical vial having a prescribed medication is aligned with (e.g., disposed directly below) the extraction door 106, and then to open the extraction door 106 to allow the patient to obtain the medical vial having the prescribed medication. The medical carousel 107 will be described in greater detail hereinbelow. The bottom compartment 102, including the medical carousel 107 and the extraction door 106 may be electronically controlled with tamper sensors and suitable locking mechanisms to ensure only authorized users may gain access to held medications.

In order to ensure that only suitably prescribed patients are dispensed appropriate medications, the disclosed medical dispenser may implement a multi-layered security system. In an embodiment, the two compartments 101, 102 of the medical dispenser 100 may be double keyed locked together to protect the bottom compartment 102, and thus the housed medical carousel 107, from unauthorized access. As disclosed above, the carousel cover 105 may be configured to securely enclose the contents of the medical carousel 107 within the carousel receptacle 138, and thus within said bottom compartment 102, as well as a GPS locator, other electronic devices and various sensors. In an embodiment, the extraction door 106 may be configured to conceal an irregularly shaped extraction aperture, such as extraction aperture 605a of FIG. 6A-6B, further impeding unauthorized access to enclosed medications. Additionally, each medical vial housed within the medical carousel 107 may be configured to engage with the medical carousel 107 using a vial flange, such as vial flange 721c of FIG. 7A, wherein the medical vial is configured to be obtained from the medical carousel 107 using an extraction tool, such as extraction tool 623 of FIG. 6A. In an embodiment, complementary embedded magnets and protrusion/depressions within the extraction tool and the vial cap, such as vial cap 321a of FIG. 3B, may be used to facilitate secure engagement between the extraction tool and medical vial, to overcome the frictional and gravitational forces needed to extract the medical vial from the medical carousel 107.

In an embodiment, the medical dispenser 100 may be configured to treat a plurality of different acute medical conditions, with the ability to select and deliver the correct treatment medication in real time from a proprietary formulary. With the diagnostic tools within the top compartment 101 and therapeutic medications stored within the bottom compartment 102, which together may assume the form of a standard sized attaché case, the physician may meet the standard of care achieved in a doctor's office setting. It should be understood that, in and embodiment, the control app may utilize a Bluetooth connection to communicate with the diagnostic devices of the top compartment 101. Furthermore, the control app may also be configured to communicate with the medical dispenser 100 through Bluetooth or other wireless connection. Alternatively, radio frequency or near field communication technologies may be employed for communication between the control app and medical dispenser, and its various components. In an embodiment, the medical dispenser 100 may be configured to run the disclosed control app without the use of a user's device, thus reducing the need for auxiliary communications devices. In an embodiment, medication inventory, device location, and other information may be transmitted from the medical dispenser to a corresponding host website for updates using Bluetooth, Wi-Fi, GPS, cellular or other communication system. Remote dispensing capabilities enabled through use of the SOUNCALINK App/control app may allow physicians to select from a plurality of different medications to treat acute medical illnesses and conditions not covered by a patient's regular daily medications. In an embodiment, a doctor that is in a different city than the patient/medical dispenser 100 may interface with the SOUNCALINK App to remotely instruct the medical dispenser 100 to dispense an appropriate medication to the patient. Various aspects and embodiments of the disclosed medical dispenser 100, and its various components, will be described hereinbelow.

In an embodiment, the top compartment 101 may be configured to house a rapid urine analysis card for use by a patient. This rapid urine analysis card may be a proprietary 3×5" card configured for use with the disclosed SOUNCALINK App. The patient may begin the test, apply the urine strip on a self-adhesive strip on the card and follow the instructions using the simple color reading system. Other manual testing devices may be provided within the top compartment of the medical dispenser 100, depending on the needs of the patient.

Figure 2A:
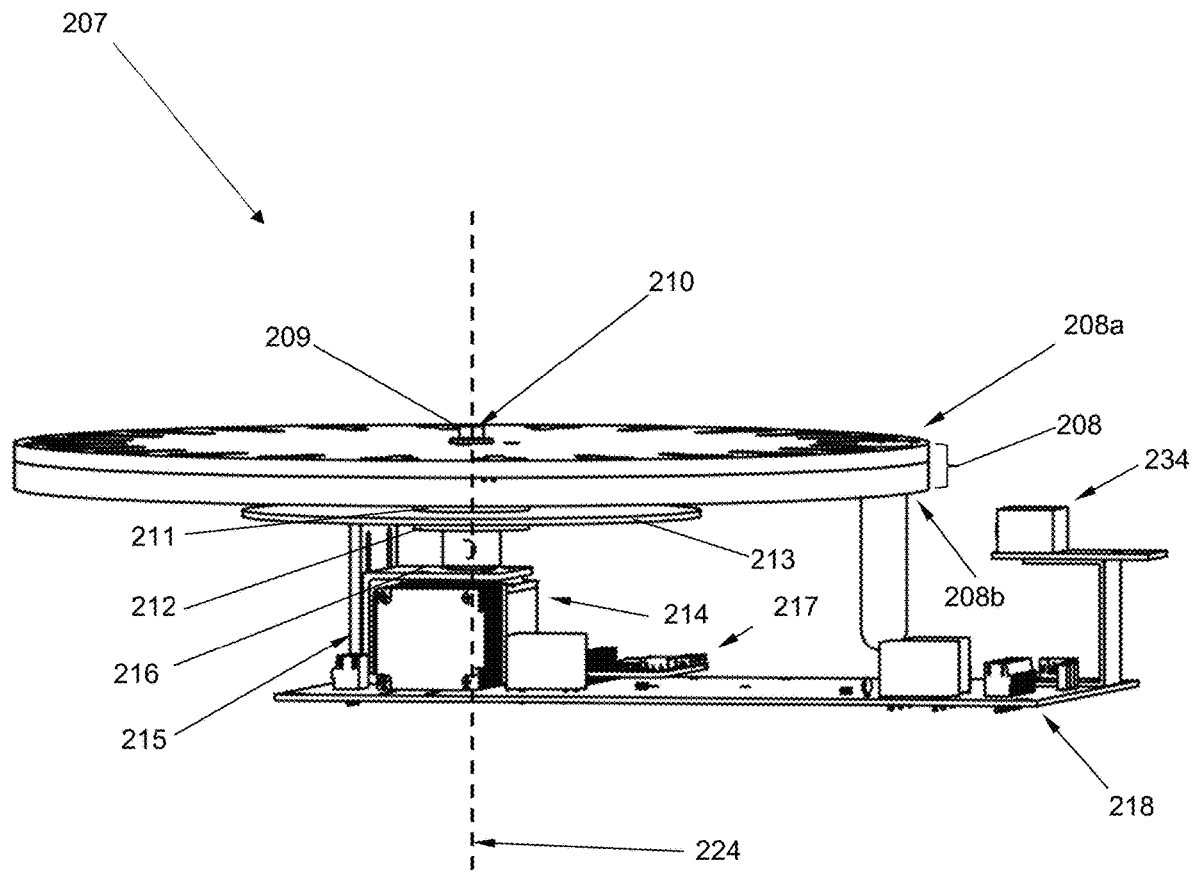
FIGS. 2A-2B illustrate the front perspective and exploded views, respectively, of a medical carousel, according to an aspect.
Figure 2B:
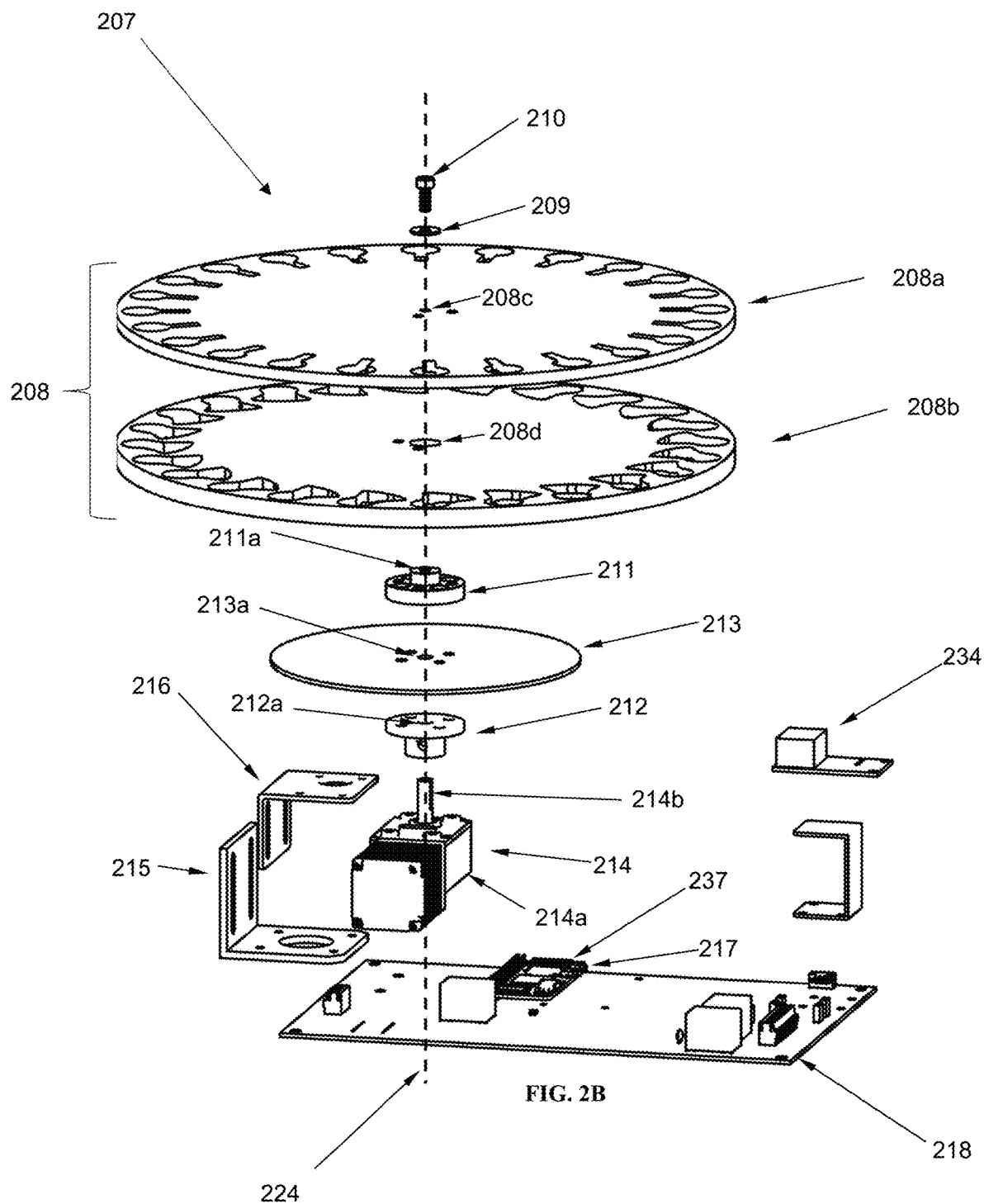

In an embodiment, the medical carousel 107 further comprises a scanner 134 configured to scan medical vials engaged with the carousel platform 108, to ensure the proper medications are dispensed, a battery pack ("backup battery") 135 configured to power the medical dispenser 100 while the medical dispenser 100 is not attached to a wall outlet, a DC connector port 136 configured to power the medical dispenser 100 using a standard wall outlet, and a SIM card shield 137, all of which may be in electrical communication with a corresponding printed circuit board, such as printed circuit board 218 of FIG. 2A-2B. The printed circuit board, SIM card shield 137 and scanner 134 will be discussed in greater detail hereinbelow. It should be understood that additional electrical elements such as wires, antennas, buttons, LEDs, a power switch, etc. may also be in electrical communication with the printed circuit board in order to enable the various functionalities of the medical dispenser 100 as described, disclosed and/or necessitated herein.

As can be seen in FIG. 1B, the medical dispenser 100 may further comprise a power cord ("power transformer") 141 in electrical communication with the medical carousel 107. This power cord 141 may be configured to be stored in the bottom compartment 102 while not in use (e.g., when not plugged into a wall outlet). In an embodiment, while stored within the bottom compartment 102, the power cord 141 may be nested within a corresponding power cord slot 140b nested within the foam liner 140, wherein power cord slot 140b is disposed outside of the carousel receptacle 138. As such, the power cord 141 may be selectively accessed to enable charging of the medical dispenser 100 as needed.

FIGS. 2A-2B illustrate the front perspective and exploded views, respectively, of a medical carousel 207, according to an aspect. As disclosed hereinabove, the medical carousel 207 may be configured to be housed within the bottom compartment of the medical dispenser, or more specifically, within a carousel receptacle nested within the bottom compartment. This medical carousel 207 may be protected within the bottom compartment by carousel cover, such as carousel cover 105 of FIG. 1A. In an embodiment, this carousel cover may be made of plexiglass or other similarly durable materials. The medical carousel 207 may be securely fastened to the bottom compartment on a printed circuit board ("PCB") 218, in order to enable suitable function of said medical carousel 207 as disclosed herein.

In an embodiment, the medical dispenser is configured to treat acute illnesses by providing patients with the correct medication for their condition, through accurate scanning of a corresponding QR/BAR code on a medical vial by one or more scanning devices attached to the PCB 218, such as a scanner 234. The appropriate medication stored within a medical vial may be delivered with a multiple component retrieval system under the supervision of a telehealth care physician/provider in communication with the patient. In an embodiment, the medical carousel 207 may comprise a PCB 218 configured to engage with the bottom compartment body, such as bottom compartment body 132 of FIG. 1A, a microprocessor 217, such as a Raspberry Pi, configured to be in electrical communication with the PCB 218, a DC connector port, such as DC connector port 136 of FIG. 1D, in electrical communication with the PCB 218, a backup battery, such as backup battery 135 of FIG. 1D, in electrical communication with the PCB 218, a mounting bracket 215 configured to engage with the PCB 218, a motor bracket 216 configured to engaged with the mounting bracket 215, and a motor 214, such as a DC worm-gear motor/worm gear motor apparatus, configured to engage with the motor bracket 216. The motor 214 may be a low voltage DC motor, which may comprise a motor body 214a configured to engage with the motor bracket 216, and a motor shaft 214b pivotally engaged with the motor body 214a, such that the motor 214 is configured to rotate the motor shaft 214b (and elements engaged with the motor shaft 214b) about a carousel rotational axis 224.

In an embodiment, the medical carousel 207 may further comprise a plurality of rotating components configured to engage with the motor shaft 214b to enable their rotation about the carousel rotational axis 224. These rotating components may include a flange coupling connector 212 configured to engage with the motor shaft 214b, an alignment/stability plate 213 disposed above and configured to engage with the flange coupling connector 212, a keyed adapter 211 disposed above and configured to engage with the alignment/stability plate 213 and a carousel platform 208 disposed above and configured to engage with the keyed adapter 211. In an embodiment, the keyed adapter 211 may be configured to support the carousel platform 208, the flange coupling connector 212 may be configured to couple the keyed adapter 211, and thus the carousel platform 208, to the motor shaft 214b, and the alignment/stability plate 213 may be configured to be compressed between the keyed adapter 211 and the flange coupling connector 212 and further configured to allow for the alignment of the medical carousel 207 within the bottom compartment without having the carousel platform 208 installed. The carousel platform 208 may be specially configured to ensure secure handling of the held medical vials, the carousel platform 208 comprising a carousel platform base 208b disposed above and engaged with the keyed adapter 211 and a carousel platform top 208a disposed above and configured to engage with the carousel platform base 208b. The mechanism through which this two layered/dual layered carousel platform 208 is configured to ensure secure handling of the held medical vials will be discussed in greater detail hereinbelow.

It should be understood that the carousel platform being "two layered" (e.g., having a carousel platform top 208a and a carousel platform base 208b) may have several advantages. In an embodiment, the multi-layered carousel platform 208 may allow for more stability on the vial vertical axis, such as vial vertical axis 325 of FIG. 3A, for each medical vial by holding each medical vial in position with two points of contact and a sufficient amount of friction, in the event that the medical apparatus is dropped or flipped upside down. In an embodiment, as will be described in greater detail hereinbelow, the carousel platform top 208a is configured to serve as a top or roof portion of a flange cavity, such as flange cavity 1026 of FIG. 10B, wherein the flange cavity is formed between the carousel platform top 208a and the carousel platform base 208b.

Figure 3A:
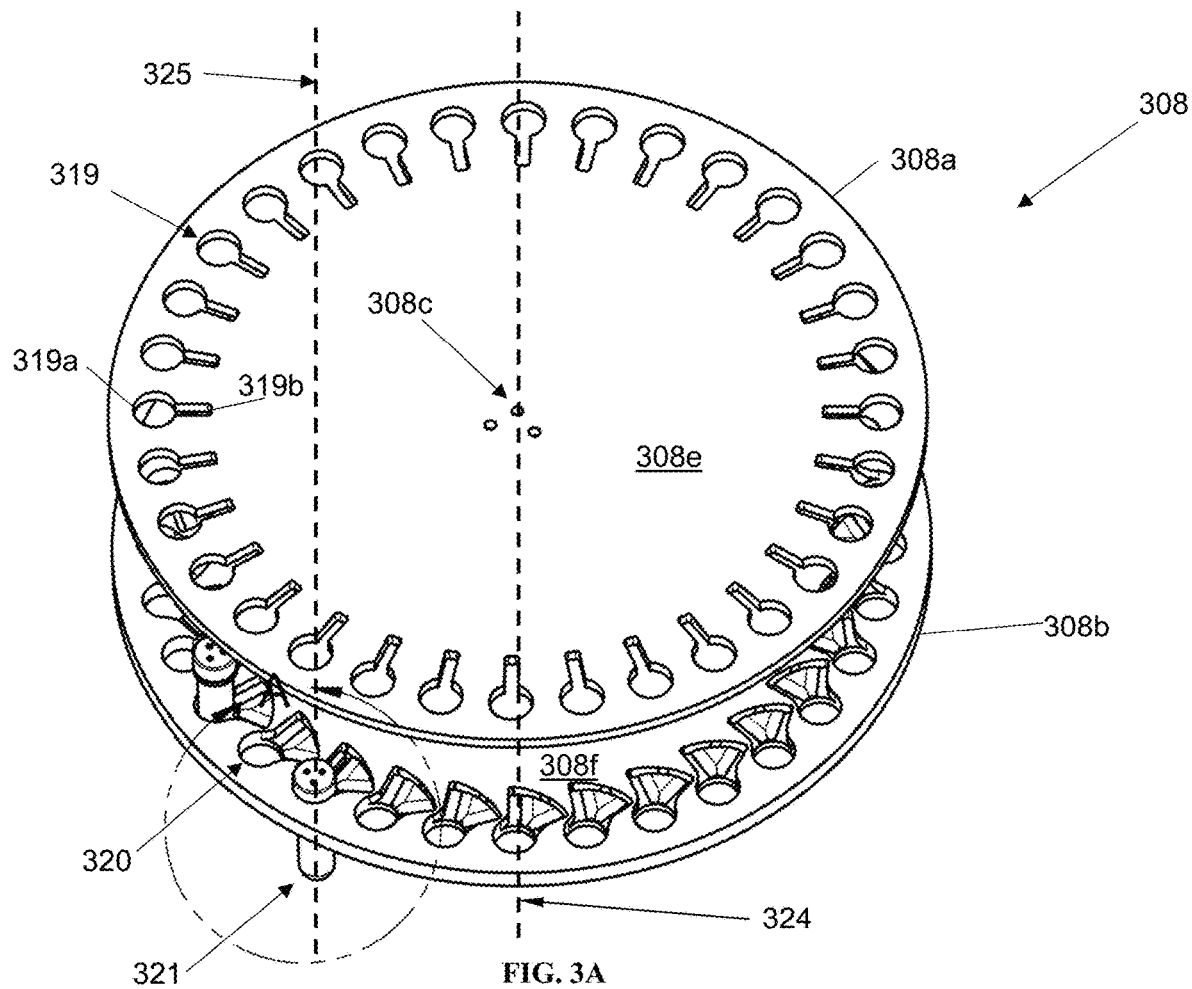
FIG. 3A illustrates the top exploded view of a carousel platform, according to an aspect.
Figure 3B:
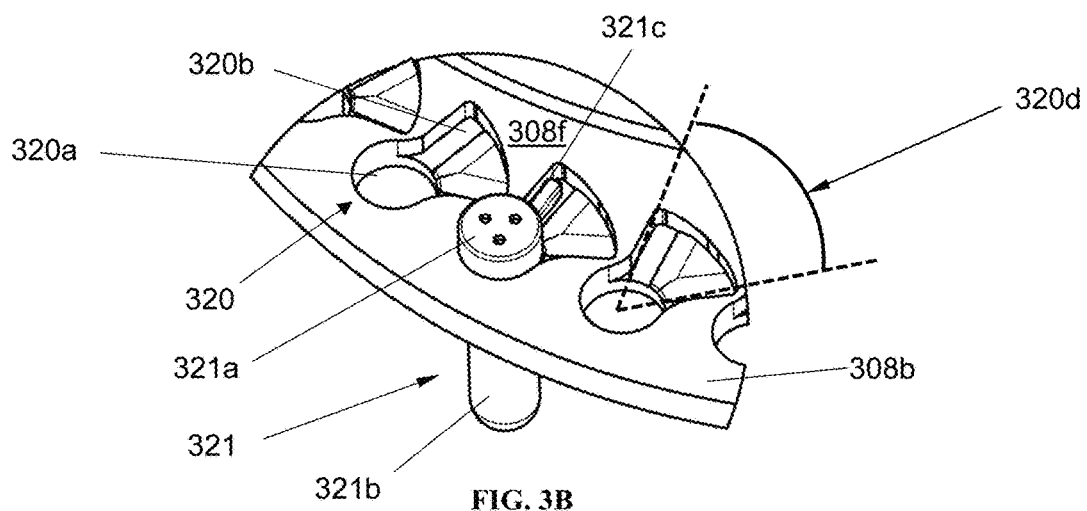
FIG. 3B illustrates the enlarged top exploded view of the carousel platform in section A of FIG. 3A, according to an aspect.
Figure 5:
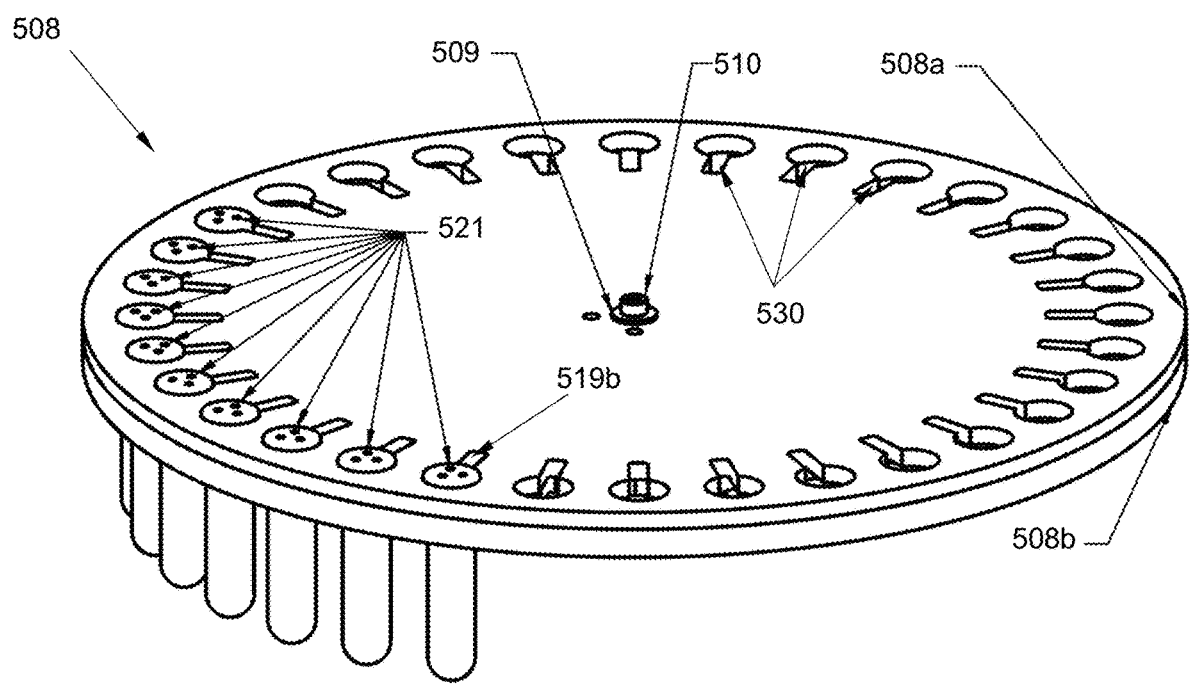
FIG. 5 illustrates the front perspective view of a carousel platform engaged with a plurality of medical vials, according to an aspect.

The disclosed embodiment of the carousel platform 208 may provide two-layered security, wherein the carousel platform base 208b has a flange channel, such as flange channel 320b of FIG. 3B, and the carousel platform top 208a has a vial port, such as vial port 319 of FIG. 3B, thus resulting in the formation of a corresponding vial holder, such as vial holder 530 of FIG. 5, within the carousel platform 208. The carousel platform may be configured such that a corresponding portion of each medical vial (e.g., a vial flange, such as vial flange 321c of FIG. 3B) may fit snuggly within the vial holder, and require precise vial manipulation to be removed from the vial holder. Furthermore, this two layered carousel platform may be configured to allow for improved rigidity on the motor shaft 214b, thus preventing flexing or deformation that may result from sample retrieval from a single layered carousel platform.

In order to secure the rotating components to the motor shaft 214b, a shaft screw 210 may be configured to nest within a central port of a shaft washer 209, as well as a corresponding mounting port within each rotating component. As such, the shaft screw 210 may be configured to nest within a flange coupling connector mounting port 212a nested within the flange coupling connector 212, an alignment/stability plate mounting port 213a nested within the alignment/stability plate 213, a keyed adapter mounting port 211a nested within the keyed adapter 211, a carousel platform base mounting port 208d nested within the carousel platform base 208b, and a carousel platform top mounting port 208c nested within the carousel platform top 208a. As is understood, the shaft screw 210 may also be configured to engage directly with the motor shaft 214b to facilitate rotation of each rotating component as described herein. Alternative structures and mechanisms may also be utilized to engage the rotating components with the motor shaft, as long as rotation of said rotating components is suitably enabled.

In order to enable the additional electronic functions disclosed herein, the medical carousel 207 may further comprise a SIM card shield 237 and a scanner 234, both of which are configured to be in electrical communication with the PCB 218. In an embodiment, the SIM card shield 237 may be configured to hold and operate a SIM phone card (cellular network) that integrates with the microprocessor 217 to receive and process coded text from a physician side of the SOUNCALINK App, to facilitate a secure connection between the medical dispenser and the doctor/provider. This coded text may be interpreted by the microprocessor 217 to select the correct medication vial from the medical carousel 207.

The interconnectivity of the microprocessor 217, motor 214, medical vial holding carousel platform 208, locking mechanisms, such as the extraction door 106 of FIG. 1, as well as the code scanning, inventorying, identification and extraction of medical vials, may be enabled via cellular, Wi-Fi and/or Bluetooth connectivity. As disclosed hereinabove, a GPS locator and a plurality of security and tamper sensors/microsensors may be configured to provide feedback on security, location, condition, inventory and any breach of device through the disclosed app. In order to enable the various functions of the disclosed medical dispenser, the microprocessor 217 may be configured to perform a variety of functions. In an embodiment, said microprocessor 217 may be configured to communicate with the disclosed control app to facilitate inventorying of medicines, status tracking, and delivery/dispensing of the medical vials. Said microprocessor 217 may also be configured to store medical information from a patient on a corresponding on-board storage unit (not shown) and facilitate doctor interaction through the control app. In an embodiment, stored patient information within the on-board storage unit may be transmitted to a doctor's system accordingly. It should be understood that the patient may not be required to have the SOUNCALINK app installed on the device or smartphone, or use of their smartphone at all, to operate the medical dispenser, as the medical dispenser may be configured to facilitate transmission of information to and from the doctor without interacting with a patient's smartphone or other devices. However, in an embodiment, the patient's smartphone and SOUNCALINK app may be required for real time video instruction on how to use the retrieval device/extraction tool, how to extract of medical vials, how to open the medical vials and further instructions for taking the dispensed medicine.

After a patient and doctor/provider interview is conducted, which may be facilitated through the utilization of the disclosed SOUNCALINK app, the doctor/provider may utilize a doctor/provider side of said SOUNCALINK app to remotely instruct the microprocessor 217 to facilitate the delivery/dispensing of the appropriate medical vial for treatment of the patient. In doing so, the microprocessor 217 is configured to actuate the motor 214 to rotate the carousel platform, such that the medical vial having the prescribed medicine is aligned with the extraction door, such that when the extraction door is open, the corresponding medical vial will be accessible to the patient. The corresponding medical vial's position may then be confirmed by the QR/barcode scanner 234 and the rotation of the carousel platform 208 may be locked for extraction of the corresponding medical vial. Upon the medical vial being confirmed to contain the prescribed medicine, the microprocessor 217 may unlock/actuate the extraction door and the patient will be able to remove the medical vial using an extraction tool, such as extraction tool 823 of FIG. 8A.

In an embodiment, a QR/Barcode scanner 234 may be utilized in the medical carousel 207 for accurately identifying medication vials and inventorying stored medicine. Each medical vial may have a corresponding QR/Barcode label on the outside surface of said medical vial, such as label 1039 of FIG. 10C. As is understood, this QR code/barcode will correlate to a medication that is held in the corresponding medical vial. Therefore, when the scanner 234 reads the corresponding label code, it will confirm the appropriate medication for inventory and verification prior to proceeding with the delivery/dispensing process. Using this method of keeping inventory and medication delivery will provide confidence that the correct prescribed medication is given to the patient for treatment.

FIG. 3A illustrates the top exploded view of a carousel platform 308, according to an aspect. FIG. 3B illustrates the enlarged top exploded view of the carousel platform 308 in section A of FIG. 3A, according to an aspect. As disclosed hereinabove, the carousel platform 308 may comprise a carousel platform base 308b and a carousel platform top 308a disposed above and configured to engage with the carousel platform base 308b. In an embodiment, the carousel platform top 308a may comprise a platform top body 308e, a plurality of vial ports 319 nested within the platform top body 308e and a carousel platform top mounting port 308c nested within the platform top body 308e and coaxially aligned with the carousel rotational axis 324. In said embodiment, the carousel platform base 308b may comprise a platform base body 308f, a plurality of vial pockets 320 nested within the platform base body 308f, and a carousel platform base mounting port, such as carousel platform base mounting port 408d of FIG. 4A, nested within the platform base body 308f and coaxially aligned with the carousel rotational axis 324.

As can be seen in FIG. 3A-4B, the carousel platform base 308b and the carousel platform top 308a may be specially configured to form a two layered carousel platform 308 to securely house a plurality of medical vials 321, while allowing patients to easily extract prescribed medicines using an appropriate extraction tool. In an embodiment, each medical vial 321 may comprise a vial body 321b, a vial cap 321a reversibly engaged with the vial body 321b and a vial flange 321c secured to and protruding from the vial body 321b. In order to facilitate secure housing of a plurality of medical vials 321, each vial pocket 320 may comprise a flange channel 320b nested within the platform base body 308f and a lower vial opening 320a associated with the flange channel 320b and nested within the platform base body 308f. It should be understood that each vial port 319 may comprise a corresponding upper vial opening 319a nested within the platform top body 308e and a flange slot 319b nested within the platform top body 308e and associated with the corresponding upper vial opening 319a.

In an embodiment, the upper vial opening 319a of each vial port 319 may be configured to be coaxially aligned with the lower vial opening 320a of a corresponding vial pocket 320 along a vial vertical axis 325, such that the vial body 321b may travel into or out of the upper and lower vial openings 319a, 320a as the medical vial is added to or removed from the carousel platform 308. It should be understood that a vial port 319 and a vial pocket 320 that are configured to align upon formation of the carousel platform 308 (e.g. a vial port 319 and vial pocket 320 configured to secure the same medical vial 321) may together be referred to as a vial holder, such as vial holder 530 of FIG. 5, for simplicity, wherein said vial holder may have a flange cavity, as disclosed hereinbelow.

As can be seen in FIG. 3B, the flange channel 320b may be configured to securely restrict the range of motion of the vial flange 321c to a corresponding flange rotation angle 320d defined by the size/angle of the flange channel 320b, while the vial flange 321c is nested within the flange channel 320b and thus the medical vial 321 is seated within the vial pocket 320. While the carousel platform top 308a is engaged with the carousel platform base 308b (e.g., the carousel platform 308 is fully formed), a flange cavity, such as flange cavity 1026 of FIG. 10B, may be formed between the platform top body 308e and the flange channel 320b. The carousel platform 308 may be configured to securely prevent each medical vial 321 from disengaging with the carousel platform 308 until the vial flange 321c is rotated to align with the flange slot 319b of the vial port 319 of the carousel platform top 308a. As will be disclosed hereinbelow, each medical vial 321 may be rotated for disengagement from (or reengagement with) the medical platform 308 through utilization of a suitable extraction tool, such as extraction tool 823 of FIG. 8A. As described hereinabove, the carousel top platform 308a may serve as a roof or top to the flange channel 320b of the carousel platform base 308b, thereby forming a flange cavity within the carousel platform 308.

Figure 4A:
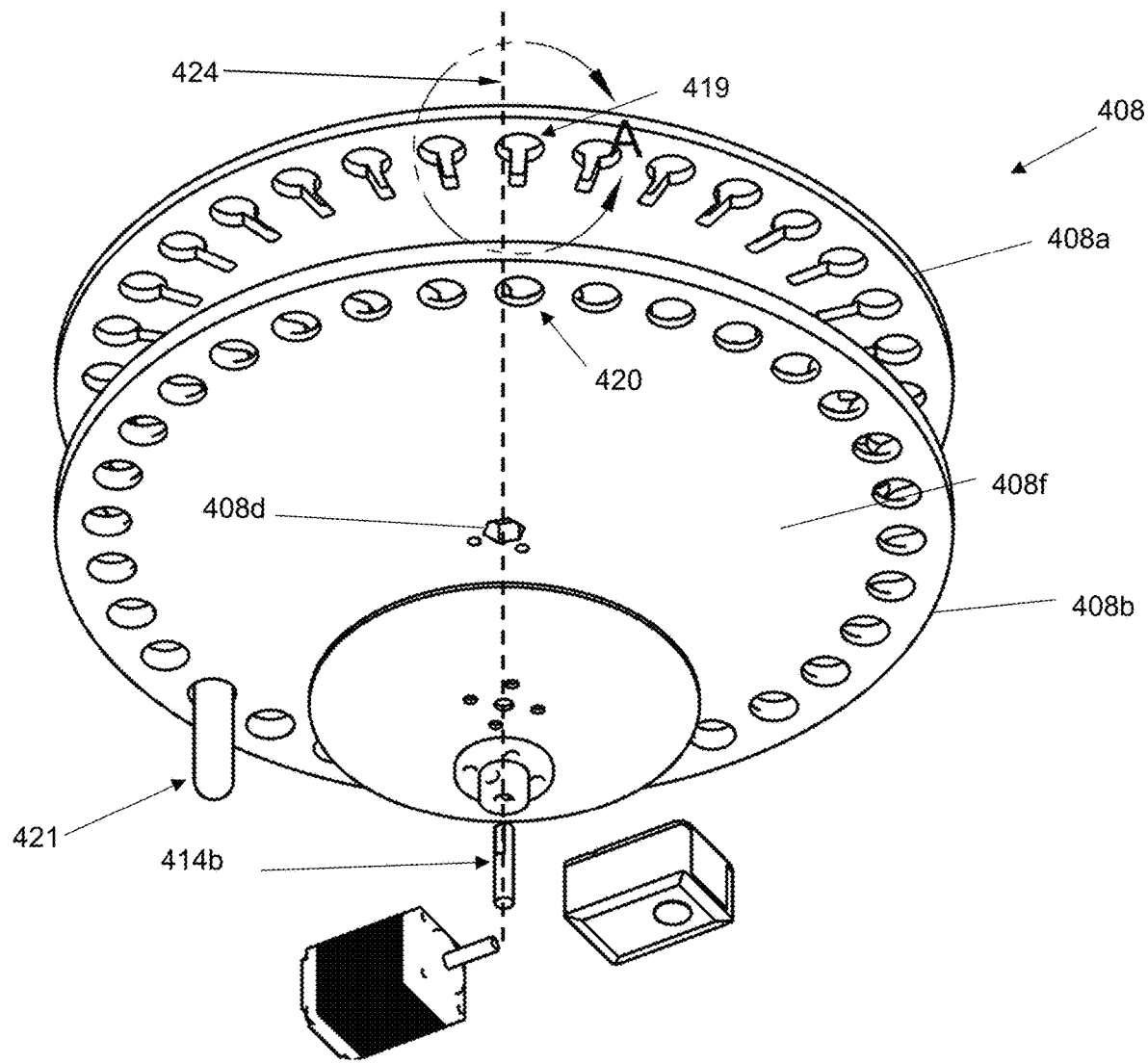
FIG. 4A illustrates the bottom exploded view of a carousel platform, according to an aspect.
Figure 4B:
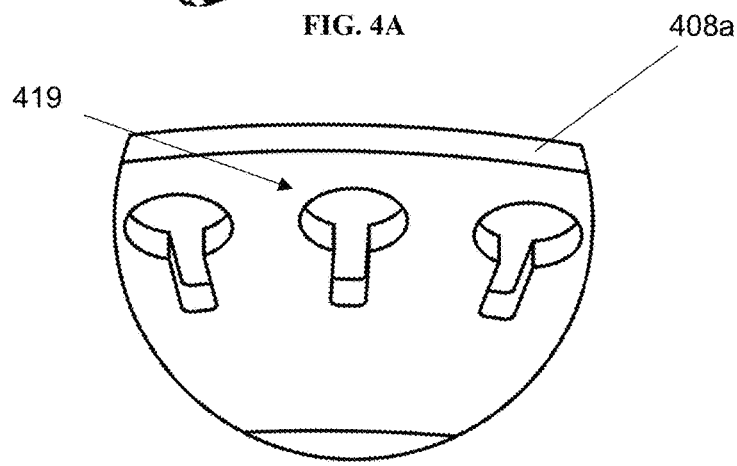
FIG. 4B illustrates the enlarged bottom exploded view of the carousel platform in section A of FIG. 4A, according to an aspect.

FIG. 4A illustrates the bottom exploded view of a carousel platform 408, according to an aspect. FIG. 4B illustrates the enlarged bottom exploded view of the carousel platform 408 in section A of FIG. 4A, according to an aspect. As disclosed hereinabove, the carousel platform 408 may comprise a carousel platform top 408a having a plurality of vial ports 419 and a carousel platform base 408b having a plurality of vial pockets 420, wherein each vial port 419 is configured to align with a corresponding vial pocket 420 to form a vial holder, wherein said vial holder is configured to securely and reversibly engage with a medical vial 421. As disclosed hereinabove, the carousel platform base 408b may comprise a platform base body 408f, a plurality of vial pockets 420 nested within the platform base body 408f, and a carousel platform base mounting port 408d nested within the platform base body 408f and coaxially aligned with the carousel rotational axis 424.

In an embodiment, the carousel platform 408 and its various elements may be made of plexiglass, plastic or a similar durable material, whereas the motor shaft 414b configured to engage with and rotate the carousel platform 408 may be made of steel or another durable material. In an embodiment, the carousel platform 408 may be configured to hold a plurality of medical vials 321, 421 in a vertical orientation, as shown in FIG. 3A-4B. In an embodiment, the carousel platform 408 may have a diameter of about 8-11.5 inches, such that said carousel platform 408 may be suitably sized to fit comfortably within the corresponding carousel receptacle, and thus the attaché case-sized medical dispenser 100 of FIG. 1A-1D. It should be understood that the particular configuration of the carousel platform 408 may facilitate the secure handling of medical vials 421 prior to and during the extraction process, which will be discussed in greater detail hereinbelow.

FIG. 5 illustrates the front perspective view of a carousel platform 508 engaged with a plurality of medical vials 521, according to an aspect. Again, the carousel platform 508 may be configured to securely hold a plurality of medical vials 521, to ensure that the contents of said medical vials 521 (e.g., medicine) are protected from tampering, accidental impacts, etc. A flange cavity, such as flange cavity 1026 of FIG. 10B, may be formed between the carousel platform top 508a and the carousel platform base 508b to help secure the medical vials 521 to the carousel platform (and thus the medical carousel). Through the use of an appropriate extraction tool, each medical vial 521 may be rotated such that its vial flange, such as vial flange 321c of FIG. 3B, aligns with (e.g., is disposed immediately below) the corresponding flange slot 519b. This alignment allows the corresponding vial flange to escape the formed flange cavity, which in turn allows the medical vial 521 to be pulled from its corresponding vial pocket and the vial ports of the carousel platform 508 for usage by a patient. In an embodiment, the carousel platform 508 may be configured to engage with the motor, such as motor 214 of FIG. 2A-2B, through the utilization of shaft screw 510 and shaft washer 509, as disclosed hereinabove.

As disclosed hereinabove, the combination of a vial port on the carousel platform top 508a with a corresponding vial pocket on the carousel platform base 508b, such as vial port 319 and vial pocket 320 of FIG. 3A, may be described as a vial holder 530, wherein each vial holder 530 is configured to secure a corresponding medical vial 521, such that said medical vial 521 may be selectively disengaged from the carousel platform 508 via rotation (e.g., clockwise or counter-clockwise rotation, depending on how the flange channels are configured) and subsequent upward/vertical lifting of the medical vial 521, as will be described in greater detail hereinbelow. It should be understood that while an authorized servicer is restocking the disclosed medical dispenser, they may be able to remove the disclosed carousel cover to replace either the entire medical carousel, such as medical carousel 207 of FIG. 2A, or just the carousel platform 508, to replace the removed medical vials once held therein. In an alternative embodiment, an authorized servicer may alternatively be able to restock each medical vial 521 through the extraction door.

Figures 6A, 6B:
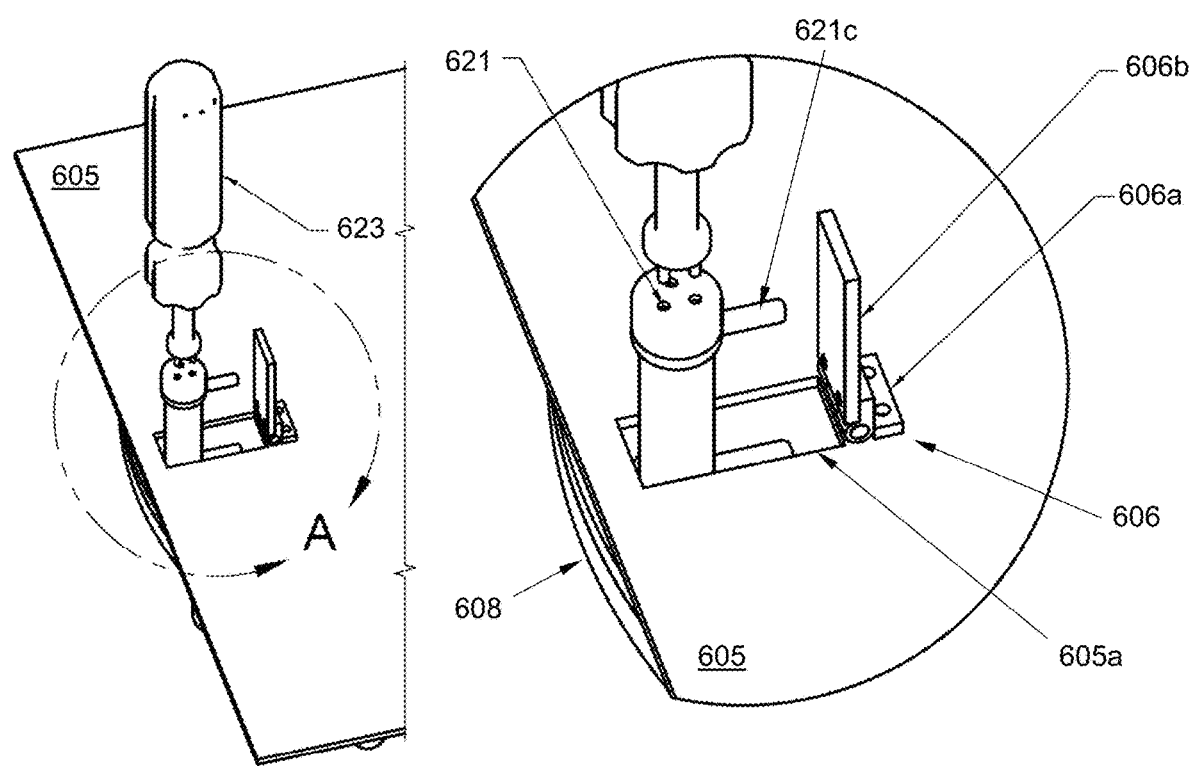
FIG. 6A illustrates a top perspective view of an extraction tool being used to retrieve a medical vial through an extraction aperture, according to an aspect.
FIG. 6B illustrates the enlarged top perspective view of the extraction tool being used to retrieve a medical vial through the extraction aperture in section A of FIG. 6A, according to an aspect.

FIG. 6A illustrates a top perspective view of an extraction tool 623 being used to retrieve a medical vial 621 through an extraction aperture 605a, according to an aspect. FIG. 6B illustrates the enlarged top perspective view of the extraction tool 623 being used to retrieve a medical vial 621 through the extraction aperture 605a in section A of FIG. 6A, according to an aspect. In an embodiment, in order for a patient to access a selected medical vial 621 having a prescribed medication, the medical carousel may need to be actuated to rotate the carousel platform 608, and thus the selected medical vial 621, such that said selected medical vial 621 is aligned with (e.g., disposed just below) the extraction aperture 605a, and the extraction door 606 needs to be actuated to open, in order to reveal the selected medical vial 621 having a prescribed medication to the patient through the extraction aperture 605a. The extraction door 606 may comprise a door hinge 606a attached to the carousel cover 605 and a door body 606b pivotally engaged with the door hinge 606a, such that the door body 606b may be selectively opened (e.g., actuated by the microprocessor) to uncover the extraction aperture 605a and expose the selected medical vial 621 to the patient.

In an embodiment, the door body 606b may be selectively locked or unlocked by a plurality of magnetic, electronic and/or other locking devices (not shown). Due to the nature and properties of the worm gear motor apparatus, such as the motor 214 of FIG. 2A-2B, stopping the carousel platform at a particular location (e.g., after a certain amount of rotation)

also acts as a locking mechanism for the carousel platform, preventing any movement during retrieval of the corresponding medical vial. The inherent locking capabilities of a worm gear motor apparatus, such as motor 214 of FIG. 2A-2B, may work in conjunction with additional locking mechanisms to prevent unauthorized rotation of the carousel platform 208, as will be described in greater detail hereinbelow.

As disclosed hereinabove, the microprocessor of the medical carousel may be configured to facilitate the selective rotation of the carousel platform 608 to align the corresponding selected medical vial underneath the extraction door 606, and upon physician/provider input, electronically open/rotate the door body 606*b* to facilitate the dispensing of a prescribed medication to a patient. As shown in FIGS. 6A-6B, an extraction tool 623 may be configured to suitably engage with a medical vial 621 to allow a patient to extract the medical vial 621 from the carousel platform 608 through the extraction aperture 605*a*. In an embodiment, the extraction tool 623 may be configured to engage with the medical vial 621 in such a way as to allow the patient to rotate the medical vial clockwise or counterclockwise, as needed, and pull the medical vial 621 upward, in order to release the vial flange 621*c* from the flange cavity, as disclosed herein. The selective engagement between the extraction tool 623 and the medical vial 621 will be described in greater detail hereinbelow.

Figure 7B:
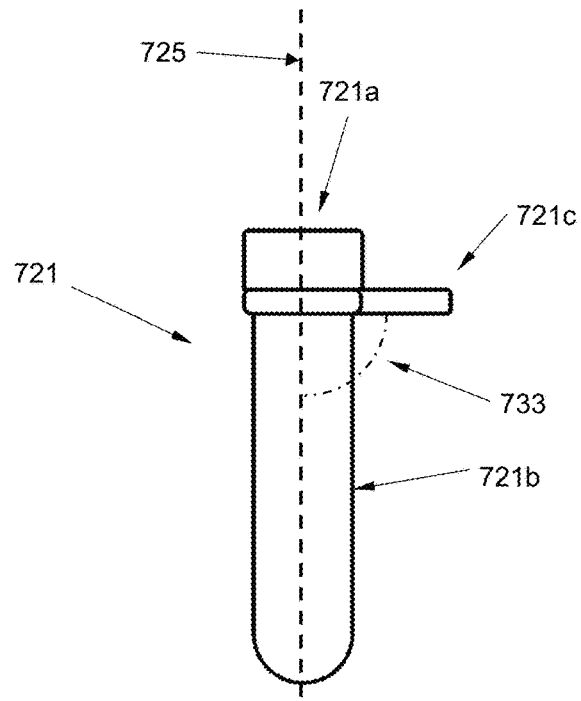
Figure 7C:
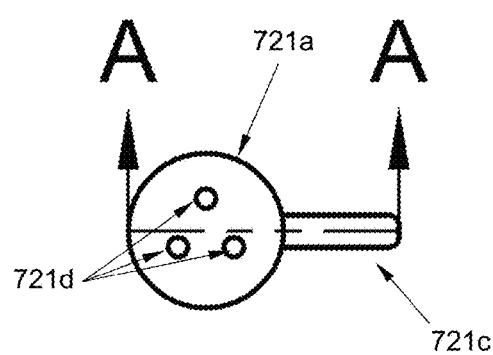
Figure 7D:
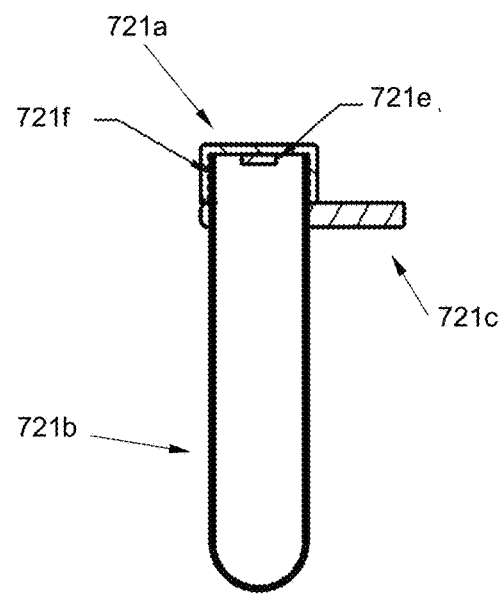
FIG. 7D illustrates a cross sectional view of a medical vial along line A-A of FIG. 7C, according to an aspect.

FIGS. 7A-7C illustrate the top perspective, side elevation and top plan views, respectively, of a medical vial 721, according to an aspect. FIG. 7D illustrates a cross sectional view of a medical vial 721 along line A-A of FIG. 7C, according to an aspect. The medical vial 721 configured for use with the disclosed medical dispenser may be configured to hold a vast variety of therapeutic medications capable of treating 80% of the top reasons that patients seek emergency room care. Each medical vial 721 may be sufficiently small to be space efficient within the medical carousel, with each medical vial 721 being configured to contain a suitable dosage of a selected medication to treat a corresponding ailment, thus potentially removing a patient's need to pursue emergency services. As disclosed hereinabove, each prescribed medical vial 721 may be dispensed to a patient in real-time, without them ever having to leave their home, hotel, or wherever the medical dispenser is located. As a result of the medications being dispensed to the patient in real-time, said patient may receive their medication immediately, and thus may experience relief much faster than having to wait to access a pharmacy after being prescribed a medication from a doctor visit. While a patient may need to access a pharmacy for medications requiring additional dosages, the medication provided by the medical dispenser may help decrease the patient's symptoms, morbidity and possibly unnecessary use of the emergency room.

As disclosed hereinabove, the medical vial 721 may comprise a vial body 721*b* configured to house medicine, a vial cap 721*a* configured to reversibly engage with the vial body 721*b* to enclose the medicine within the medical vial 721 and a vial flange 721*c* affixed with, secured to or otherwise engaged with the vial body 721*b*, wherein the vial flange 721*c* is configured to protrude away from the vial vertical axis 725 and the vial body 721*b*. In an embodiment, the vial flange 721*c* may protrude away from the vial vertical axis 725, such that a flange angle 733 formed between the vial vertical axis 725 and the vial flange 721*c* is about 90 degrees (e.g., the vial flange 721*c* may be perpendicular to the vial vertical axis 725, and thus perpendicular to the vial body 721*b*). In an embodiment, in order to enable the extraction of a medical vial 721 from the medical carousel using a corresponding extraction tool, a plurality of pin ports 721*d* may be nested within the vial cap 721*a*, to enable engagement between the sample vial 721 and the disclosed extraction tool, such as extraction tool 823 of FIG. 8A. In order to ensure a secure, selective engagement between the vial cap 721*a* and the vial body 721*b* is established, an engagement thread 721*f* may be disposed on the vial body 721*b* to allow the vial body 721*b* to better grip the vial cap 721*a*. The medical vial 721 may further comprise a vial magnet 721*e* associated with the vial cap 721*a*, such that said vial magnet 721*e* is configured to magnetically engage with a corresponding extraction tool magnet, such as extraction tool magnet 823*e* of FIG. 8D, to improve further improve engagement between the extraction tool and the medical vial to allow for medical vial extraction from the medical carousel.

Figure 8A:
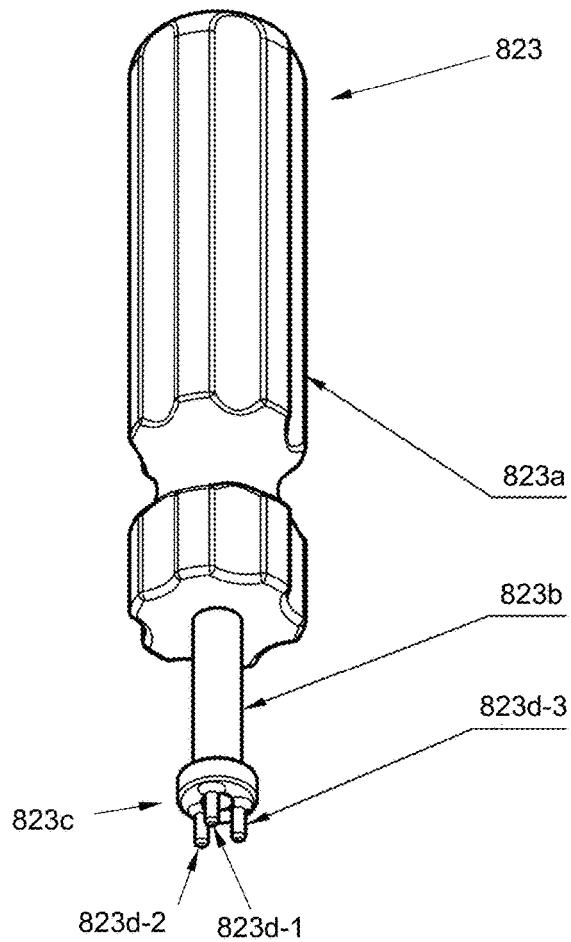
FIGS. 8A-8C illustrate the front perspective, side elevation and top plan views, respectively, of an extraction tool, according to an aspect.

In an alternative embodiment, instead of having a plurality of pin ports 721 nested within the vial cap 721*a*, at least one recession/depression or protrusion may be provided in/on the vial cap 721*a*, wherein the extraction tool, such as extraction tool 823 of FIG. 8A, is configured to have a complementary protrusion or recession/depression to engage with recession/depression or protrusion on the vial cap 721*a*. In an embodiment, a singular depression having a unique shape may be nested within the vial cap 721*a*, whereas the extraction tool may have a complementarily shaped (and suitably sized) protrusion configured to be nested within the singular depression to facilitate selective engagement between the extraction tool and the vial cap 721*a*. In another embodiment, a plurality of protrusions may extend from the vial cap 721*a*, whereas the extraction tool may have a plurality of complementarily positioned (and suitably sized) recesses, wherein each recess is configured to surround a corresponding protrusion to facilitate selective engagement between the extraction tool and the vial cap 721*a*. In another embodiment, the vial cap 721*a* may have a unique keyed structure having a combination of protrusions and depressions, whereas the extraction tool may have complementarily placed and sized depressions and protrusions for engagement with those of the vial cap 721*a*, thus facilitating secure engagement between the extraction tool and vial cap 721*a*. More complex depression and/or protrusion patterns may be utilized on the vial cap 721*a*, with corresponding complementary protrusion and/or depression patterns on the extraction tool, to make unauthorized extraction of the medical vials more difficult. As long as compatible engaging/mating structures are disposed on the vial cap 721*a* and extraction tool, suitable extraction of the medical vial 721 from the medical carousel may be facilitated.

In an embodiment, a medical dispenser, such as medical dispenser 100 of FIG. 1A, may be suitably stocked with medications configured to treat common ailments. In said embodiment, the medical dispenser may contain 30-36 different medications, wherein said medications are prescription or over-the-counter medications. In an embodiment, the medical dispenser may be configured to carry no controlled substances. As disclosed hereinabove, each medical vial 721 may be stamped with an identifiable code, such as a QR or BAR code for easy identification by a code scanner within the medical dispenser, such as scanner 234 of FIG. 2A. In an embodiment, the medical vials 721 may be plastic, or another suitably durable, inert material.

Figure 8B:
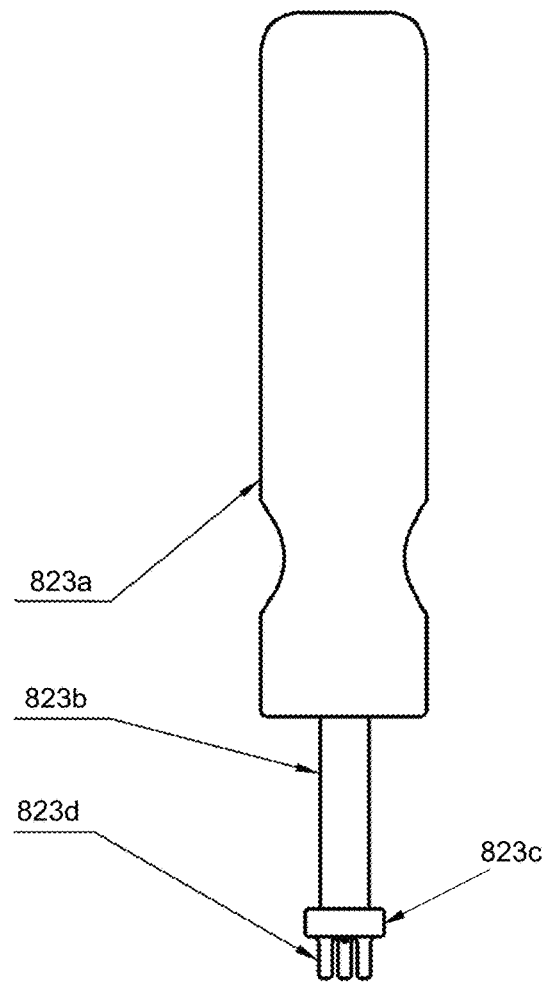
Figure 8C:
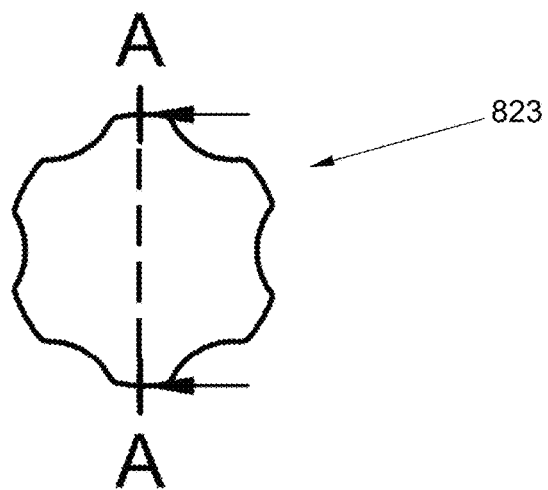
Figure 8D:
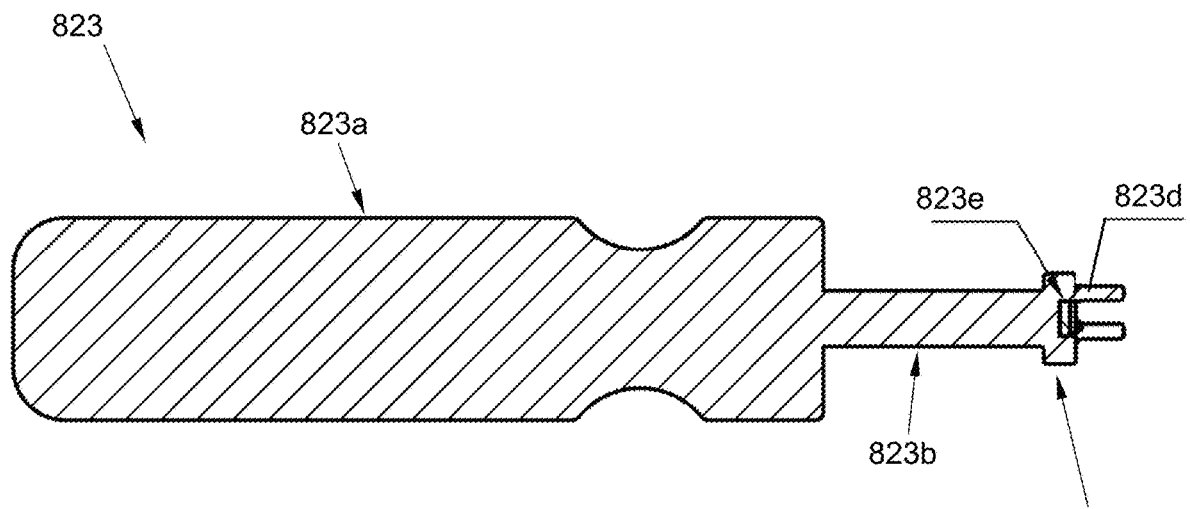
FIG. 8D illustrates the cross-sectional view of the extraction tool along line A-A of FIG. 8C, according to an aspect.

FIGS. 8A-8C illustrate the front perspective, side elevation and top plan views, respectively, of an extraction tool 823, according to an aspect. FIG. 8D illustrates the cross-sectional view of the extraction tool 823 along line A-A of FIG. 8C, according to an aspect. As disclosed hereinabove, an extraction tool 823 may be utilized by a patient to extract a medical vial from a corresponding medical dispenser. In an embodiment, the extraction tool 823 may comprise a handle 823*a*, a shaft 823*b* attached to or otherwise engaged with the handle 823*a*, a tool head 823*c* attached to or otherwise engaged with the shaft 823*b*, a plurality of extraction pins 823*d*-1, 823*d*-2, 823*d*-3 attached to or otherwise engaged with the tool head 823*c* and an extraction tool magnet 823*e* embedded/nested within or otherwise engaged with the tool head 823*c*. In said embodiment, the plurality of extraction pins may comprise a first extraction pin 823*d*-1, a second extraction pin 823*d*-2, and a third extraction pin 823*d*-3. It should be understood that the placements of the extraction pins 823*d* on the tool head 823*c* are configured to be complementary to the placements of the pin ports of each medical vial, such as pin ports 721*d* of FIG. 7A. In an embodiment, the shaft 823*b*, tool head 823*c*, and extraction pins 823*d* may all be made out of aluminum, or another suitably strong and durable, non-ferrous material.

Figure 9A:
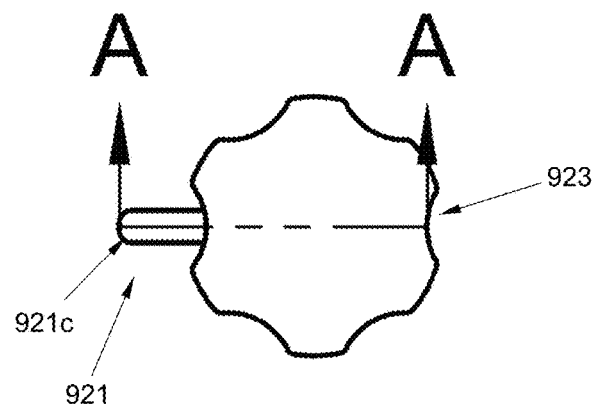
FIG. 9A illustrates the top plan view of an extraction tool engaging with a medical vial, according to an aspect.
Figure 9C:
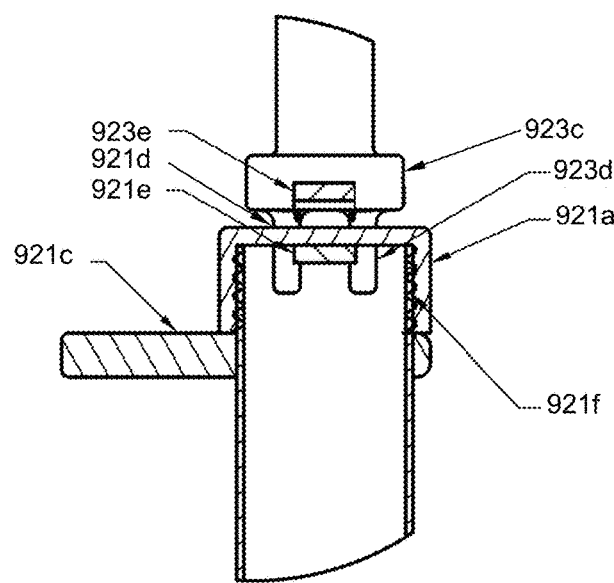
FIG. 9C illustrates the enlarged cross-sectional view of the extraction tool engaging with a medical vial in section B of FIG. 9B, according to an aspect.
Figure 9B:
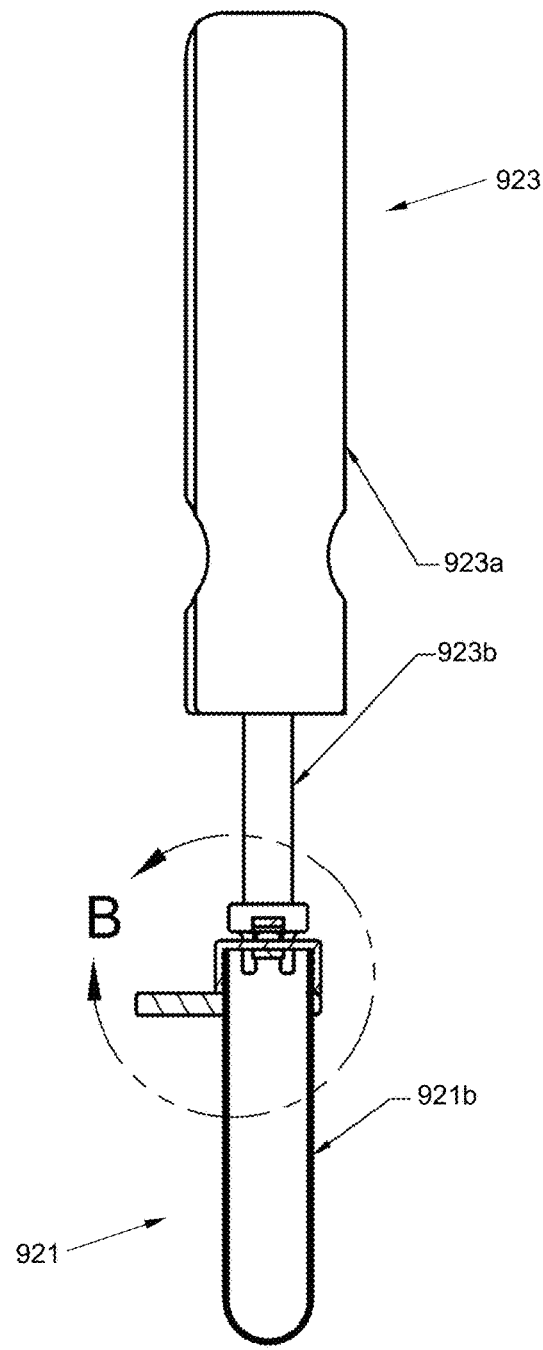
FIG. 9B illustrates the side cross-sectional view of the extraction tool engaging with a medical vial along line A-A of FIG. 9A, according to an aspect.

FIG. 9A illustrates the top plan view of an extraction tool 923 engaging with a medical vial 921, according to an aspect. FIG. 9B illustrates the side cross-sectional view of the extraction tool 923 engaging with a medical vial 921 along line A-A of FIG. 9A, according to an aspect. FIG. 9C illustrates the enlarged cross-sectional view of the extraction tool 923 engaging with a medical vial 921 in section B of FIG. 9B, according to an aspect. As has been described hereinabove, the extraction tool 923 is configured to engage with a medical vial 921 secured within a medical carousel in order to allow a patient to extract a prescribed medicine held within the medical vial 921. As shown in FIG. 9C, each extraction pin 923*d* on the extraction tool 923 may be configured to be inserted into a complementary pin port 921*d* nested within the vial cap 921*a* of the medical vial 921. The insertion of these extraction pins 923*d* within corresponding pin ports 921*d* allows the patient to easily rotate the medical vial 921 engaged with medical carousel through manual rotation of the extraction tool handle 923*a*, thus rotating the vial flange 921*c* within the corresponding flange cavity, such as flange cavity 1026 of FIG. 10B, to align the vial flange 921*c* with the flange slot of the corresponding vial port, such as flange slot 319*b* of FIG. 3A.

While the engagement between the extraction pins 923*d* with the pin ports 921*d* may allow the patient to easily rotate the medical vial 921, in order to allow the patient to actually pull the medical vial out of the medical carousel, a pair of complementary magnets on the extraction tool 923 and the medical vials 921 may be utilized. In an embodiment, the extraction tool magnet 923*e* associated with the extraction tool 923 may be configured to magnetically engage with the vial magnet 921*e* associated with the vial cap 921*a* of the medical vial 921. This magnetic engagement may be configured to provide a sufficiently strong, but reversible engagement between the extraction tool 923 and the medical vial 921, such that after rotating the medical vial 921 to align the vial flange 921*c* with the corresponding flange slot, the patient may simply pull the extraction tool upward to utilize the magnetic attraction between the vial magnet 921*e* and the extraction tool magnet 923*e* to remove the medical vial 921 from the medical dispenser.

In an embodiment, the extraction pins 923*d* on the tool head 923*c* and pin ports 921*d* on the vial cap 921*a* may be configured to enable rotation of the medical vial 921 and its vial flange 921*c*, whereas the extraction tool magnet 923*e* and the vial magnet 921*e* may be configured to enable the lifting of the medical vial out of the medical carousel after the rotation is performed. The process of extracting a medical vial 921 from the medical carousel using the extraction tool 923 will be described in greater detail hereinbelow. It should be understood that each magnet (e.g., the extraction tool magnet 923*e* and the vial magnet 921*e*) may be suitably encased within a resin or plastic material within its respective structure, to protect it from damage while still allowing said magnets 921*e*, 923*e* to exert attractive forces upon each other. It should be understood that the magnets 921*e*, 923*e* are configured such that the attractive forces experienced between the extraction tool magnet 923*e* and the vial magnet 921*e* may be sufficiently strong to overcome the frictional forces exerted on the medical vial 921 by the carousel platform, as well as the gravitation forces exerted on the medical vial 921 by gravity, thus allowing for vertical extraction of the medical vial 921 from the corresponding vial holder.

Figure 10A:
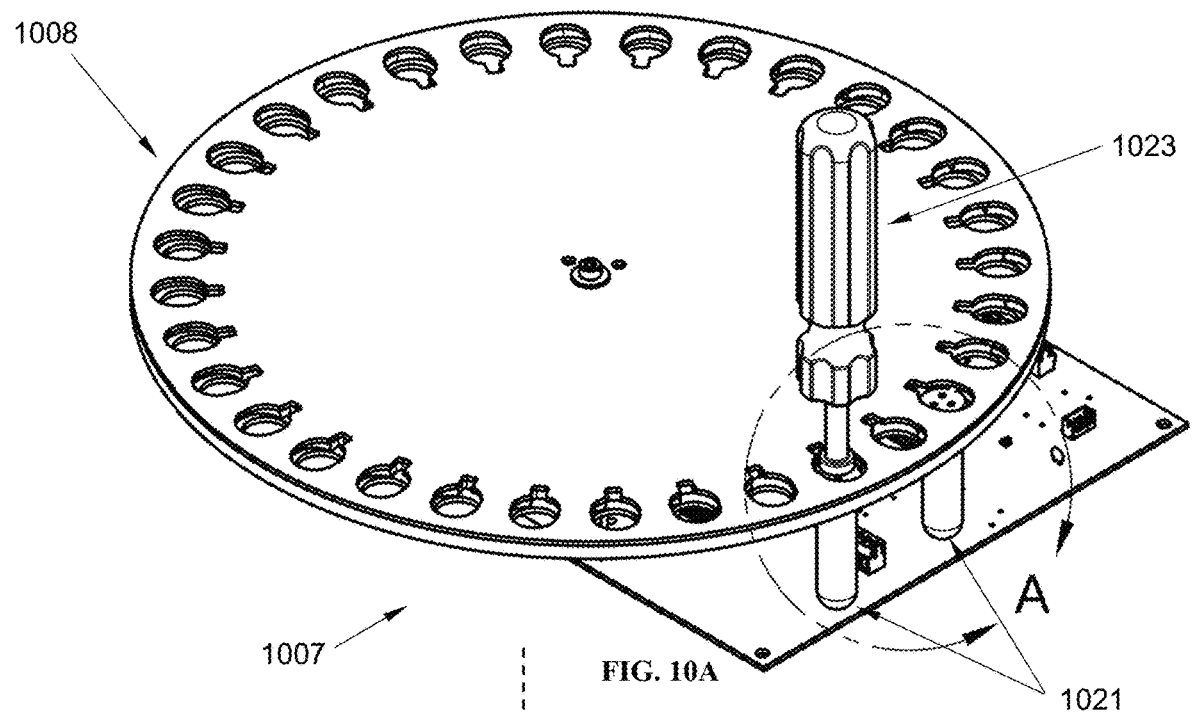
FIG. 10A illustrates the top perspective view of an extraction tool being used to retrieve a medical vial from a medical carousel, according to an aspect.
Figure 10B:
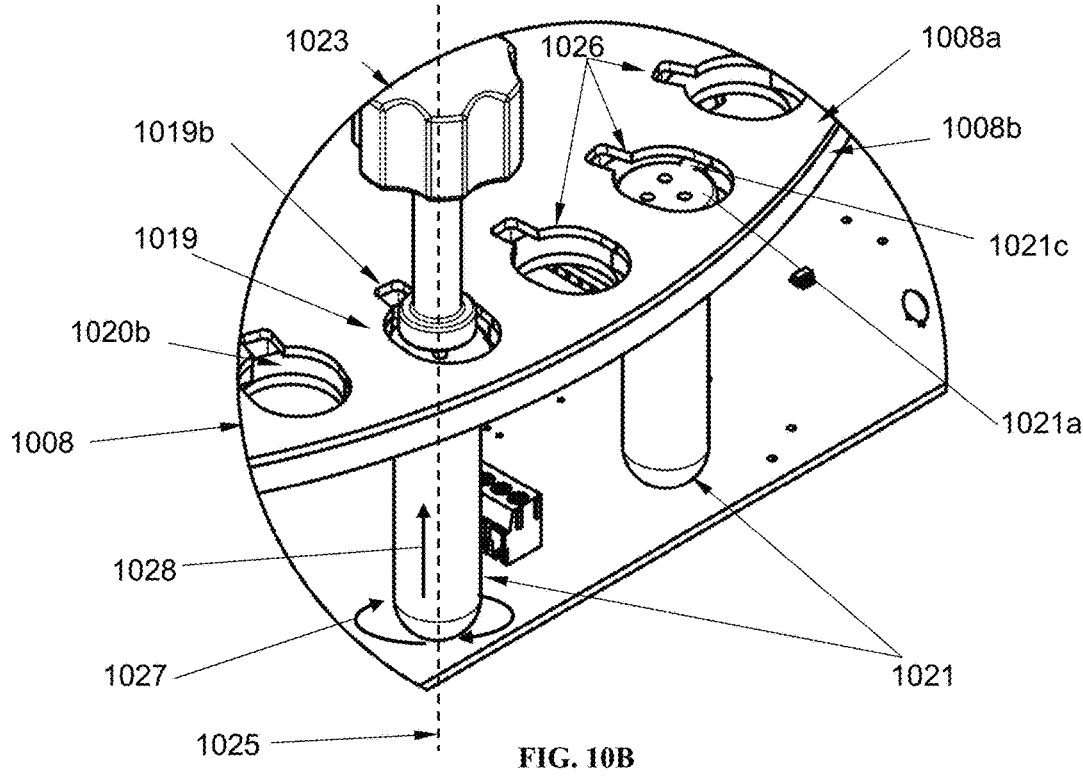
FIG. 10B illustrates the enlarged top perspective view of the extraction tool being used to retrieve a medical vial from the medical carousel in section A from FIG. 10A, according to an aspect.
Figure 10C:
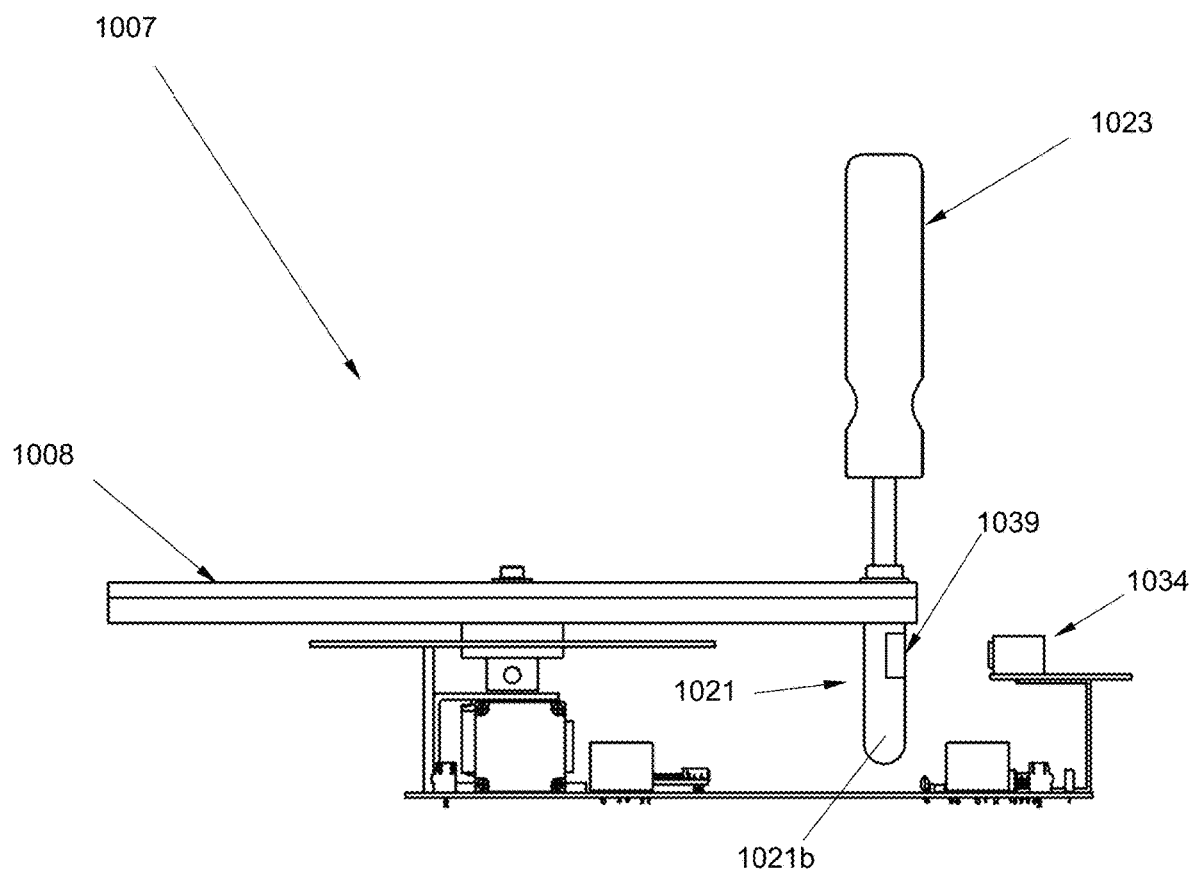
FIG. 10C illustrates the front elevation view of an extraction tool being used to retrieve a medical vial from a medical carousel, according to an aspect.

FIG. 10A illustrates the top perspective view of an extraction tool 1023 being used to retrieve a medical vial 1021 from a medical carousel 1007, according to an aspect. FIG. 10B illustrates the enlarged top perspective view of the extraction tool 1023 being used to retrieve a medical vial 1021 from the medical carousel 1007 in section A from FIG. 10A, according to an aspect. FIG. 10C illustrates the front elevation view of an extraction tool 1023 being used to retrieve a medical vial 1021 from a medical carousel 1007, according to an aspect. As disclosed hereinabove, the extraction tool 1023 is configured to engage securely with a medical vial 1021 in order to enable rotational movement of the medical vial 1021 to rotate the vial flange 1021*c* within the flange cavity 1026, such that the vial flange 1021*c* aligns with the flange slot 1019*b*. Furthermore, the extraction tool 1023 is also configured to engage securely with the medical vial 1021 to enable vertical extraction of the medical vial 1021 from the medical carousel 1007 by sliding the vial flange 1021*c* upwards out of the flange cavity 1026 through the flange slot 1019*b* of the vial port 1019, to allow the medical vial 1021 to be extracted from the medical carousel 1007 for use. Again, the flange cavity 1026 formed between the carousel platform top 1008*a* and the carousel platform base 1008*b* is configured to securely hold a medical vial 1021 in place within the medical dispenser until a user rotates said medical vial 1021 for extraction using the extraction tool 1023, accordingly.

In an embodiment, the combination of the extraction pins from the extraction tool 1023 engaging with/nesting within the pin ports of the medical vial 1021 and the extraction tool magnet magnetically engaging with the vial magnet, may be configured to enable rotational movement 1027 and vertical (upward) movement 1028 of the medical vial 1021, accordingly. As described hereinabove, each vial holder may comprise a flange cavity 1026 configured to surround and selectively confine a corresponding vial flange 1021*c* while the medical vial 1021 is secured to the corresponding vial holder, and a flange slot 1019*b* associated with and in communication with the flange cavity 1026, such that the flange slot 1019*b* and flange cavity 1026 form a continuous hollow portion within the carousel platform 1008. As stated hereinabove, the carousel platform top, such as carousel platform top 308*a* of FIG. 3A, may act as a roof/top to form the flange cavity 1026, helping to selectively secure the flange of a corresponding medical vial 1021 within said flange cavity 1026.

Depending on the size and the shape of the flange channel 1020*b* within the carousel platform base 1008*b* (and thus the formed flange cavity 1026), the amount of rotational movement required to rotate the medical vial 1021 into a position wherein it may be vertically extracted may vary. In an embodiment having a flange channel similar to that of FIG. 3B, the patient may need to rotate the medical vial 1021 along the arc formed by the flange rotation angle, such as flange rotation angle 320*d* of FIG. 3B, about a corresponding vial vertical axis 1025 to align the corresponding vial flange 1021*c* with the flange slot 1019*b* to enable vertical extraction of the medical vial 1021 as described herein. In an embodiment, the flange rotation angle, such as flange rotation angle 320*d* of FIG. 3B, may be between about 30 and about 90 degrees.

As disclosed hereinabove, each medical vial 1021 may have a corresponding label 1039 on it in order to allow the scanner 1034 to easily identify its contents. Each label 1039 may be disposed on the outer surface of the vial body 1021*b*, such that said label 1039 may be easily detected by the scanner 1034 as the carousel platform 1008 rotates. In an embodiment, each label 1039 may include a bar code, QR code, or other label type identifiable by a scanner, for verification of medical vial contents prior to dispensing. In this way the dispensing of the proper medication may be facilitated through multiple safeguards, including the specific positioning of a corresponding medical vial within the medical carousel 1007 while stocking/restocking and scanning of a corresponding label 1039 prior to opening the extraction door, such as extraction door 606 of FIG. 6B.

The combination of features recited for the disclosed medical dispenser are configured to provide patients with a mechanism to quickly attain relief for an ailment without having to wait for or travel to healthcare facilities or a pharmacy. Through the utilization of the disclosed medical carousel, medications may be securely held and appropriately dispensed based upon a remote doctor's assessment of a patient's health.

Figure 11A:
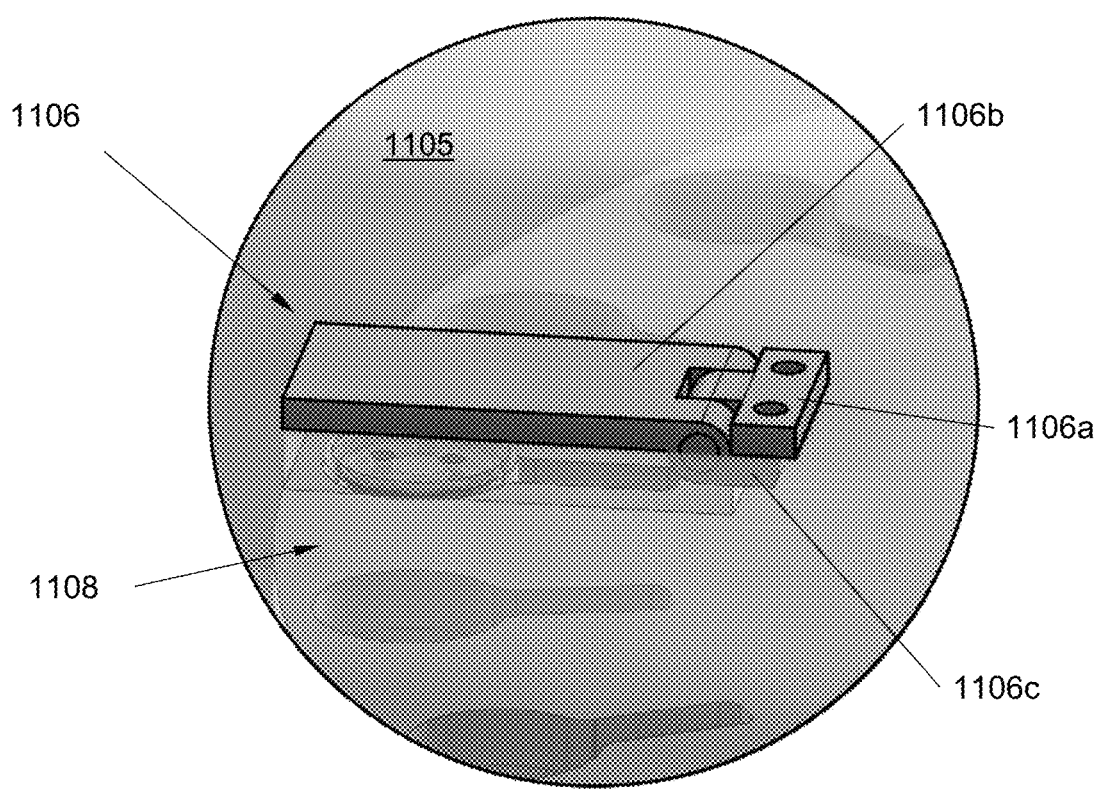
FIG. 11A illustrates the front perspective view of an extraction door in the closed position, according to an aspect.
Figure 11B:
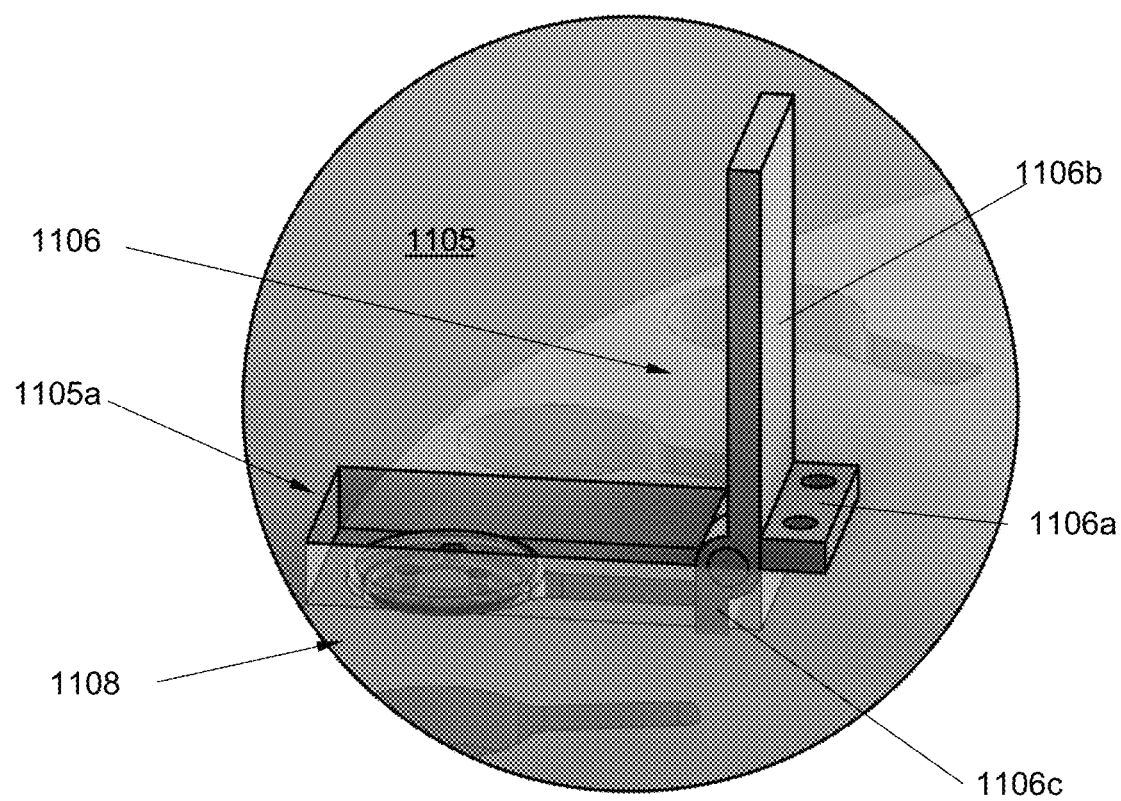
FIG. 11B illustrates the front perspective view of an extraction door in the open position, according to an aspect.

FIG. 11A illustrates the front perspective view of an extraction door 1106 in the closed position, according to an aspect. FIG. 11B illustrates the front perspective view of an extraction door in the open position, according to an aspect. As described hereinabove, the extraction door 1106 may comprise a door hinge 1106*a* attached to the carousel cover 1105 and a door body 1106*b* pivotally engaged with the door hinge 1106*a*, such that the door body 1106*b* may selectively cover the extraction aperture 1105*a* nested in the carousel cover 1105. In an embodiment, the extraction door 1106 may further comprise a platform stopper 1106*c* attached to the door body 1106*b*, wherein the platform stopper 1106*c* may be configured to rotate with the door body 1106*b*. In an embodiment, the door body 1106*b* and platform stopper 1106*c* may form a monolithic structure that is pivotally engaged with the door hinge 1106*a*, such that a lever/teeter-totter like structure is formed, wherein the rigid structure of the door body 1106*b* (the major/larger side of the fulcrum) and platform stopper 1106*c* (the minor/smaller side of the fulcrum) may rotate about its engagement with the door hinge 1106*a*.

As can be seen in the embodiment of FIG. 11B, the lever type mechanism formed by the extraction door 1106 may be configured such that as the extraction door 1106 is opened, the door body 1106*b* may point away from the carousel platform 1108, whereas the platform stopper 1106*c* may point toward the carousel platform 1108. Furthermore, while the extraction door 1106 is in the "opened" orientation of FIG. 11B, the platform stopper 1106*c* may directly contact the carousel platform 1108. By directly contacting the carousel platform 1108 while the extraction door 1106 is in the opened orientation, the platform stopper 1106*c* may be configured to further prevent rotation of the carousel platform 1108 while the extraction door 1106 is opened. In an embodiment, both the direct engagement (mechanical hold) of the platform stopper 1106*c* with the carousel platform 1108 while the extraction door 1106 is opened, and the worm drive motor apparatus, such as motor 214 of FIG. 2B, used to rotate the carousel platform 1108, may be configured to prevent unauthorized rotation of the carousel platform 1108. As such, once the motor rotates the carousel platform 1108 to the designated position, and the extraction door is opened to engage the platform stopper 1106*c* with the carousel platform 1108, the carousel platform 1108 may thus be locked into position, such that further rotation of the carousel platform 1108 while the carousel door 1106 is opened is highly unlikely, or at least is significantly more difficult.

Figure 12A:
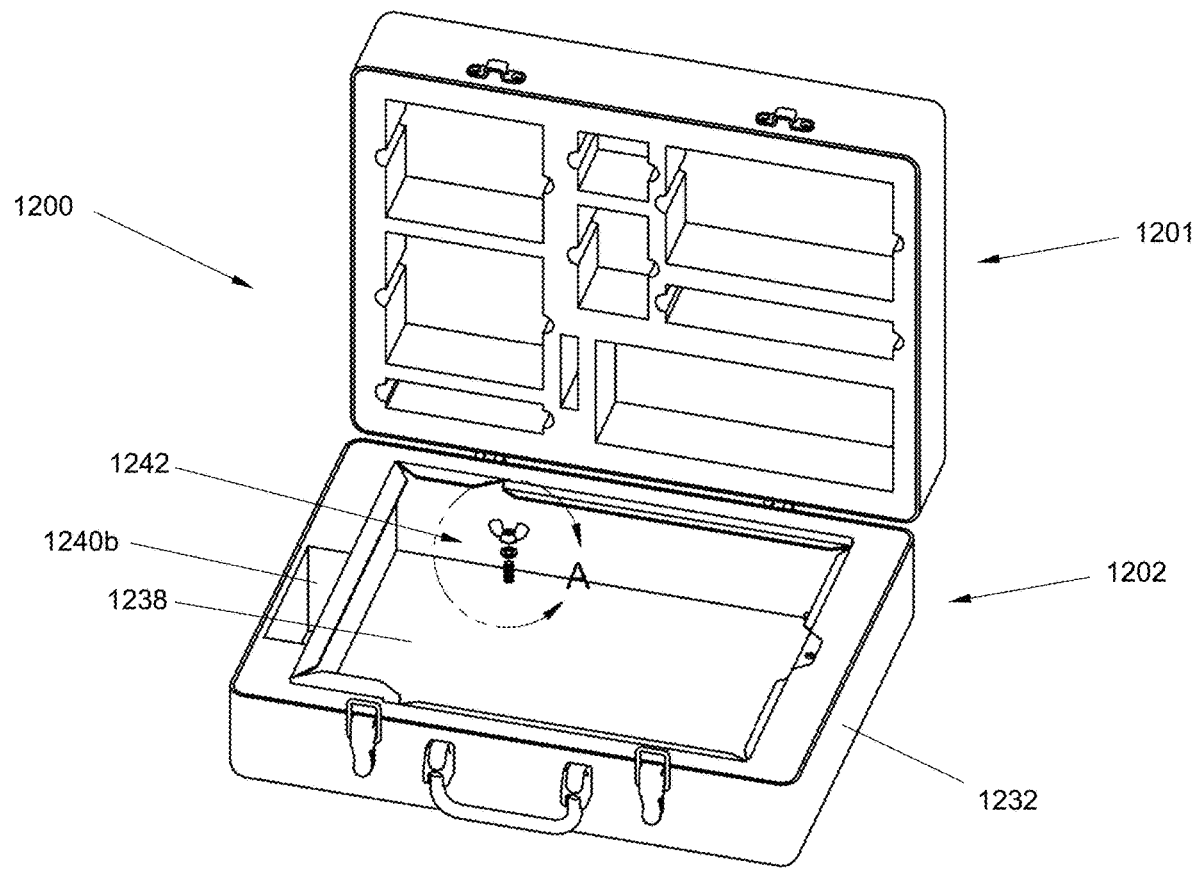
FIG. 12A illustrates the front perspective view of a carousel receptacle being engaged with the bottom compartment body, according to an aspect.
Figure 12B:
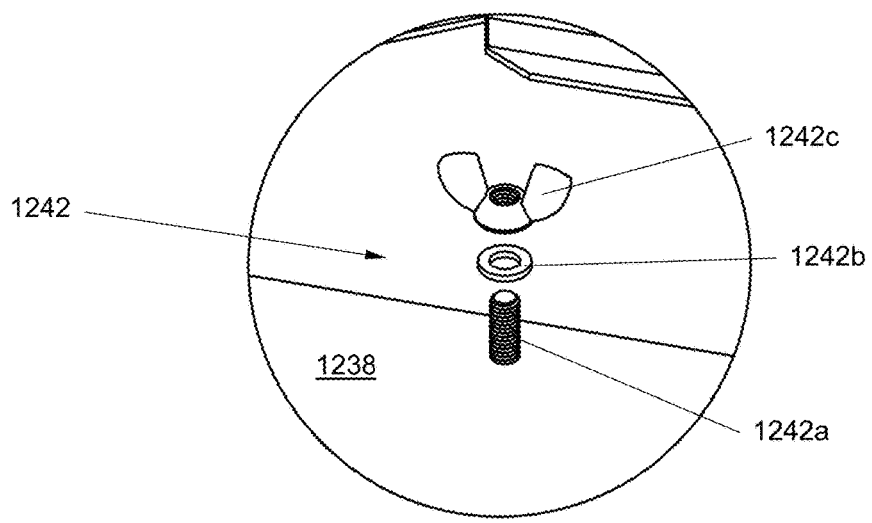
FIG. 12B illustrates the front perspective view of a carousel receptacle being engaged with the bottom compartment body in section A from FIG. 12A, according to an aspect.

FIG. 12A illustrates the front perspective view of a carousel receptacle 1238 being engaged with the bottom compartment body 1232, according to an aspect. FIG. 12B illustrates the front perspective view of a carousel receptacle 1238 being engaged with the bottom compartment body 1232 in section A from FIG. 12A, according to an aspect. In an embodiment, the top compartment 1201 may be pivotally engaged with the bottom compartment 1202, to form a structure similar in shape to an attaché case. In said embodiment, a power cord slot 1240*b* may be nested within the bottom compartment 1202. As disclosed hereinabove, the carousel receptacle 1238 may be attached to the bottom compartment body 1232 by at least one corresponding flat lock 1242. In an embodiment, each flat lock 1242 may comprise a bolt 1242*a*, such as a square nut carriage bolt, configured to be threaded through both the bottom compartment body 1232 and the carousel receptacle 1238, a bolt nut 1242*c* configured to engage with the corresponding bolt 1242*a* from within the carousel receptacle 1238 and a bolt washer 1242*b* engaged with the corresponding bolt 1242 and disposed between the carousel receptacle 1238 and the bolt nut 1242*c*.

In an embodiment, the head of the bolt (not shown) that is accessible on the outside surface of the medical dispenser 1200 may be configured to be tamper proof or tamper resistant, such that attempted manipulation of the bolt 1242*a* may not influence the engagement between the bolt 1242*a* and the bolt nut 1242*c*. Furthermore, the bolt nut 1242*c* may only be accessed by authorized users, due to its disposition within the carousel receptacle 1238, thus requiring removal of the carousel cover 1205 in order to be accessed. This feature allows for the carousel receptacle 1238 to remain securely attached to the bottom compartment body 1232 when appropriate, but also provides a mechanism for authorized users to remove and/or replace the carousel receptacle (and a contained medical carousel) as necessary. In an embodiment, the carousel receptacle 1238 may be secured to the bottom compartment body 1232 by up to four flat locks 1242, each flat lock having a square neck carriage bolt as their bolt 1242*a*. In an alternative embodiment, a different quantity or flat locks 1242 or alternative structures may be utilized to facilitate secure engagement between the carousel receptacle 1238 and the bottom compartment body 1232.

It may be advantageous to set forth definitions of certain words and phrases used in this patent document. The term "couple" and its derivatives refer to any direct or indirect communication between two or more elements, whether or not those elements are in physical contact with one another. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

Further, as used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims.

If present, use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

The term "medical vial" may be used to describe any receptacle, container, enclosure, and the like, that may store a medication within.

Throughout this description, the aspects, embodiments or examples shown should be considered as exemplars, rather than limitations on the apparatus or procedures disclosed or claimed. Although some of the examples may involve specific combinations of method acts or system elements, it should be understood that those acts and those elements may be combined in other ways to accomplish the same objectives.

Acts, elements and features discussed only in connection with one aspect, embodiment or example are not intended to be excluded from a similar role(s) in other aspects, embodiments or examples.

Aspects, embodiments or examples of the invention may be described as processes, which are usually depicted using a flowchart, a flow diagram, a structure diagram, or a block diagram. Although a flowchart may depict the operations as a sequential process, many of the operations can be performed in parallel or concurrently. In addition, the order of the operations may be re-arranged. With regard to flowcharts, it should be understood that additional and fewer steps may be taken, and the steps as shown may be combined or further refined to achieve the described methods.

If means-plus-function limitations are recited in the claims, the means are not intended to be limited to the means disclosed in this application for performing the recited function, but are intended to cover in scope any equivalent means, known now or later developed, for performing the recited function.

Claim limitations should be construed as means-plus-function limitations only if the claim recites the term "means" in association with a recited function.

If any presented, the claims directed to a method and/or process should not be limited to the performance of their steps in the order written, and one skilled in the art can readily appreciate that the sequences may be varied and still remain within the spirit and scope of the present invention.

Although aspects, embodiments and/or examples have been illustrated and described herein, someone of ordinary skills in the art will easily detect alternate of the same and/or equivalent variations, which may be capable of achieving the same results, and which may be substituted for the aspects, embodiments and/or examples illustrated and described herein, without departing from the scope of the invention. Therefore, the scope of this application is intended to cover such alternate aspects, embodiments and/or examples. Hence, the scope of the invention is defined by the accompanying claims and their equivalents. Further, each and every claim is incorporated as further disclosure into the specification.

The invention claimed is:

1. A medical apparatus comprising:
    a top compartment having a plurality of foam pockets configured to securely house diagnostic devices;
    a bottom compartment configured to be pivotally engaged with the top compartment, the bottom compartment comprising:
        a bottom compartment body;
        a carousel receptacle nested within the bottom compartment body;
        a plurality of medical vials configured to be selectively nested within the carousel receptacle, each medical vial of the plurality of medical vials having:
            a vial body;
            a vial cap configured to be selectively engaged with the vial body to secure a medication within the vial body; and
            a vial flange affixed to the vial body, wherein the vial flange is configured to protrude away from a vial vertical axis, forming about a 90 degree flange angle to the vial vertical axis; and
        a medical carousel configured to be nested within the carousel receptacle and selectively engaged with the plurality of medical vials, the medical carousel comprising:
            a two layered carousel platform having:
                a plurality of vial holders, wherein each vial holder is configured to be selectively engaged with a corresponding medical vial of the plurality of medical vials, each vial holder of the plurality of vial holders comprising:
                    a flange cavity configured to selectively confine the vial flange of a corresponding medical vial of the plurality of medical vials, such that the vial flange of the corresponding medical vial is securely nested within the flange cavity; and
                    a flange slot associated with the flange cavity, wherein the flange slot is configured to allow the vial flange of the corresponding medical vial to be selectively removed from the flange cavity upon rotation of the corresponding medical vial about the corresponding vial vertical axis; and
                a motor configured to be pivotally engaged with the carousel platform, the motor being further configured to selectively rotate the carousel platform about a carousel rotational axis;
            a carousel cover configured to be engaged with the carousel receptacle, such that the medical carousel is enclosed within the carousel receptacle, the carousel cover having an extraction aperture; and
            an extraction door attached to the carousel cover, wherein the extraction door is configured to selectively cover the extraction aperture; and
        an extraction tool configured to be inserted through the extraction aperture to selectively engage with a corresponding medical vial of the plurality of medical vials for selective extraction of the corresponding medical vial from the medical carousel.

2. The medical apparatus of claim 1, wherein the top compartment further comprises a plurality of diagnostic devices, wherein each diagnostic device of the plurality of diagnostic devices is configured to be nested within a corresponding foam pocket of the plurality of foam pockets.

3. The medical apparatus of claim 2, wherein the medical apparatus is configured to transmit data collected from the plurality of diagnostic devices to a doctor.

4. The medical apparatus of claim 1, wherein the medical apparatus receives a command issued from a doctor's device to actuate the motor to rotate the carousel platform to align a selected medical vial having a prescribed medication with the extraction aperture and then actuate the extraction door to expose the selected medical vial to a patient in real-time.

5. The medical vial of claim 1, further comprising a plurality of pin ports nested within the vial cap and a vial magnet engaged with the vial cap.

6. The medical apparatus of claim 5, the extraction tool comprising a handle, a shaft attached to the handle, a tool head attached to the shaft, a plurality of extraction pins attached to the tool head, and an extraction tool magnet engaged with the tool head, wherein each extraction pin of the plurality of extraction pins is configured to be selectively nested within a corresponding pin port of the plurality of pin ports and the extraction tool magnet is configured to be magnetically engaged with the vial magnet, in order to facilitate selective rotation and lifting of a corresponding medical vial.

7. The medical apparatus of claim 1, wherein the extraction tool is configured to allow a patient to rotate the vial flange within the flange cavity, and lift the vial flange out of the flange cavity through the flange slot to facilitate removal of a corresponding medical vial of the plurality of medical vials from a corresponding vial holder of the plurality of vial holders.

8. The medical apparatus of claim 1, further comprising a scanner associated with the medical carousel, wherein the scanner is configured to scan a corresponding label disposed on a corresponding medical vial of the plurality of medical vials to identify a medication disposed within the corresponding medical vial.

9. A medical apparatus comprising:
a bottom compartment body;
a carousel receptacle nested within the bottom compartment body;
a plurality of medical vials configured to be selectively nested within the carousel receptacle, each medical vial of the plurality of medical vials having:
  a vial body;
  a vial cap configured to be selectively engaged with the vial body to secure a medication within the vial body; and
  a vial flange secured to the vial body, wherein the vial flange is configured to protrude away from a vial vertical axis; and
a medical carousel configured to be nested within the carousel receptacle and selectively engaged with the plurality of medical vials, the medical carousel comprising:
  a carousel platform having:
    a plurality of vial holders, wherein each vial holder is configured to be selectively engaged with a corresponding medical vial of the plurality of medical vials, each vial holder of the plurality of vial holders comprising:
      a flange cavity configured to selectively confine a vial flange of a corresponding medical vial of the plurality of medical vials, such that the vial flange of the corresponding medical vial is nested within the flange cavity; and
      a flange slot associated with the flange cavity, wherein the flange slot is configured to allow the vial flange of the corresponding medical vial to be selectively removed from the flange cavity upon rotation of the corresponding medical vial about the corresponding vial vertical axis; and
    a motor pivotally engaged with the carousel platform, the motor being further configured to selectively rotate the carousel platform on a carousel rotational axis;
  a carousel cover engaged with the carousel receptacle, such that the medical carousel is enclosed within the carousel receptacle, the carousel cover having an extraction aperture; and
  an extraction door attached to the carousel cover, wherein the extraction door is selectively covers the extraction aperture.

10. The medical apparatus of claim 9, wherein the medical apparatus is configured to receive a command issued from a doctor's device to actuate the motor to rotate the carousel platform to align a selected medical vial having a prescribed medication with the extraction aperture and then actuate the extraction door to expose the selected medical vial to a patient.

11. The medical vial of claim 9, further comprising a plurality of pin ports nested within the vial cap and a vial magnet engaged with the vial cap.

12. The medical apparatus of claim 11, further comprising an extraction tool configured to be selectively engaged with a corresponding medical vial, the extraction tool comprising a handle, a shaft attached to the handle, a tool head attached to the shaft, a plurality of extraction pins attached to the tool head, and an extraction tool magnet engaged with the tool head, wherein each extraction pin of the plurality of extraction pins is configured to be selectively nested within a corresponding pin port of the plurality of pin ports and the extraction tool magnet, magnetically engaged with the vial magnet, in order to facilitate selective rotation and lifting of the corresponding medical vial.

13. The extraction door of claim 9 comprising a door hinge attached to the carousel cover, a door body pivotally engaged with the door hinge and a platform stopper attached to the door body, wherein the door body is configured to be selectively rotated such that the extraction aperture is uncovered and the platform stopper engages directly with the carousel platform.

14. The medical apparatus of claim 9, further comprising a scanner associated with the medical carousel, wherein the scanner is configured to scan a corresponding label disposed on a corresponding medical vial of the plurality of medical vials to identify a medication disposed within the corresponding medical vial.

15. A medical apparatus comprising:
a plurality of medical vials, each medical vial of the plurality of medical vials having:
  a vial body;
  a vial cap configured to be selectively engaged with the vial body to secure a medication within the vial body;
  a vial flange affixed to the vial body, wherein the vial flange is configured to extend away from a vial vertical axis;
  a plurality of pin ports nested within the vial cap;
  a vial magnet engaged with the vial cap; and a medical carousel configured to be selectively engaged with the plurality of medical vials, the medical carousel comprising:
- a carousel platform having:
  - a plurality of vial holders, wherein each vial holder of the plurality of vial holders is configured to be selectively engaged with a corresponding medical vial of the plurality of medical vials, each vial holder of the plurality of vial holders comprising:
    - a flange cavity configured to selectively confine a vial flange of a corresponding medical vial, such that the vial flange of the corresponding medical vial is nested within the flange cavity; and
    - a flange slot associated with the flange cavity, wherein the flange slot is configured to allow the vial flange of the corresponding medical vial to be selectively removed from the flange cavity upon rotation of the corresponding medical vial about the corresponding vial vertical axis.

16. The medical apparatus of claim 15, further comprising an extraction tool configured to selectively engage with a corresponding medical vial of the plurality of medical vials, the extraction tool comprising a handle, a shaft attached to the handle, a tool head attached to the shaft, a plurality of extraction pins attached to the tool head, and an extraction tool magnet engaged with the tool head, wherein each extraction pin of the plurality of extraction pins is configured to be selectively nested within a corresponding pin port of the plurality of pin ports and the extraction tool magnet is configured to be magnetically engaged with the vial magnet, in order to facilitate selective rotation and lifting of the corresponding medical vial.

17. The medical apparatus of claim 15, wherein the medical carousel further comprises a printed circuit board in electrical communication with the motor, a SIM card shield in electrical communication with the printed circuit board, and a microprocessor in electrical communication with the printed circuit board.

18. The medical apparatus of claim 15, wherein the medical apparatus is configured to allow a patient to access a selected medical vial of the plurality of medical vials, the selected medical vial containing a prescribed medication, upon receiving a corresponding signal from a doctor.

19. The medical apparatus of claim 15, further comprising a scanner associated with the medical carousel, wherein the scanner is configured to scan a corresponding label disposed on a corresponding medical vial of the plurality of medical vials to identify a medication disposed within the corresponding medical vial.

* * * * *